United States Patent
Wu et al.

(10) Patent No.: US 9,593,204 B2
(45) Date of Patent: Mar. 14, 2017

(54) BRANCHED POLYMERIC EMULSIFIERS

(71) Applicant: Lubrizol Advanced Materials, Inc., Cleveland, OH (US)

(72) Inventors: Anchuu Wu, Broadview Heights, OH (US); Douglas M. Barr, Monroe, GA (US); Nancy S. Marchant, Medina, OH (US); Ashoke K. Sengupta, Frisco, TX (US); Feng-Lung Gorden Hsu, Cleveland, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 14/423,151

(22) PCT Filed: Aug. 8, 2013

(86) PCT No.: PCT/US2013/054103
§ 371 (c)(1),
(2) Date: Feb. 23, 2015

(87) PCT Pub. No.: WO2014/031353
PCT Pub. Date: Feb. 27, 2014

(65) Prior Publication Data
US 2015/0218312 A1    Aug. 6, 2015

Related U.S. Application Data

(60) Provisional application No. 61/692,303, filed on Aug. 23, 2012.

(51) Int. Cl.
| | |
|---|---|
| C08G 65/22 | (2006.01) |
| C08G 65/28 | (2006.01) |
| C08G 65/332 | (2006.01) |
| C08G 65/26 | (2006.01) |
| C07H 15/04 | (2006.01) |
| C08G 65/34 | (2006.01) |
| A61K 8/60 | (2006.01) |
| A61Q 19/00 | (2006.01) |
| A61K 8/86 | (2006.01) |
| A61K 8/06 | (2006.01) |
| B01F 17/00 | (2006.01) |
| A61K 8/92 | (2006.01) |

(52) U.S. Cl.
CPC .......... *C08G 65/3322* (2013.01); *A61K 8/062* (2013.01); *A61K 8/608* (2013.01); *A61K 8/86* (2013.01); *A61K 8/92* (2013.01); *A61Q 19/00* (2013.01); *B01F 17/0028* (2013.01); *C07H 15/04* (2013.01); *C08G 65/22* (2013.01); *C08G 65/2609* (2013.01); *C08G 65/332* (2013.01); *C08G 65/34* (2013.01); *A61K 2800/10* (2013.01); *A61K 2800/54* (2013.01); *C08G 2650/26* (2013.01); *C08G 2650/30* (2013.01); *C08G 2650/54* (2013.01); *C08G 2650/64* (2013.01)

(58) Field of Classification Search
None
See application file for complete search history.

(56) References Cited

U.S. PATENT DOCUMENTS

| | | | |
|---|---|---|---|
| 8,778,864 B2 * | 7/2014 | Andjelic | A61K 8/39 510/467 |
| 2010/0144978 A1 | 6/2010 | Bevinakatti et al. | |
| 2012/0122755 A1 | 5/2012 | Andjelic et al. | |
| 2013/0310530 A1 | 11/2013 | Jha et al. | |

FOREIGN PATENT DOCUMENTS

| | | |
|---|---|---|
| DE | 102010029628 A1 | 12/2010 |
| DE | 102011003090 A1 | 7/2012 |
| WO | 2010/063155 A1 | 6/2010 |

OTHER PUBLICATIONS

SAA Pedia, "Polyglyceryl Methylglucose Distearate—Surfactants", retrieved from Internet http://www.saapedia.org/en/saa?type=detail&id=4439, Nov. 16, 2012.

* cited by examiner

*Primary Examiner* — Eric Olson
(74) *Attorney, Agent, or Firm* — Thoburn T. Dunlap

(57) ABSTRACT

The present invention relates to esterified glycerylated alkyl glycoside and to a process for making same. The esterified glycerylated alkyl glycoside have one or more polyglyceryl moieties and one or more acyl moieties, wherein all of the one or more acyl moieties are situated on the one or more polyglyceryl moieties via an ester linkage. These compounds have been found to be useful as emulsifiers and coemulsifiers in the formulation of a phase stable emulsions suitable for use in personal care, home care, industrial and institutional, and health care applications.

32 Claims, 1 Drawing Sheet

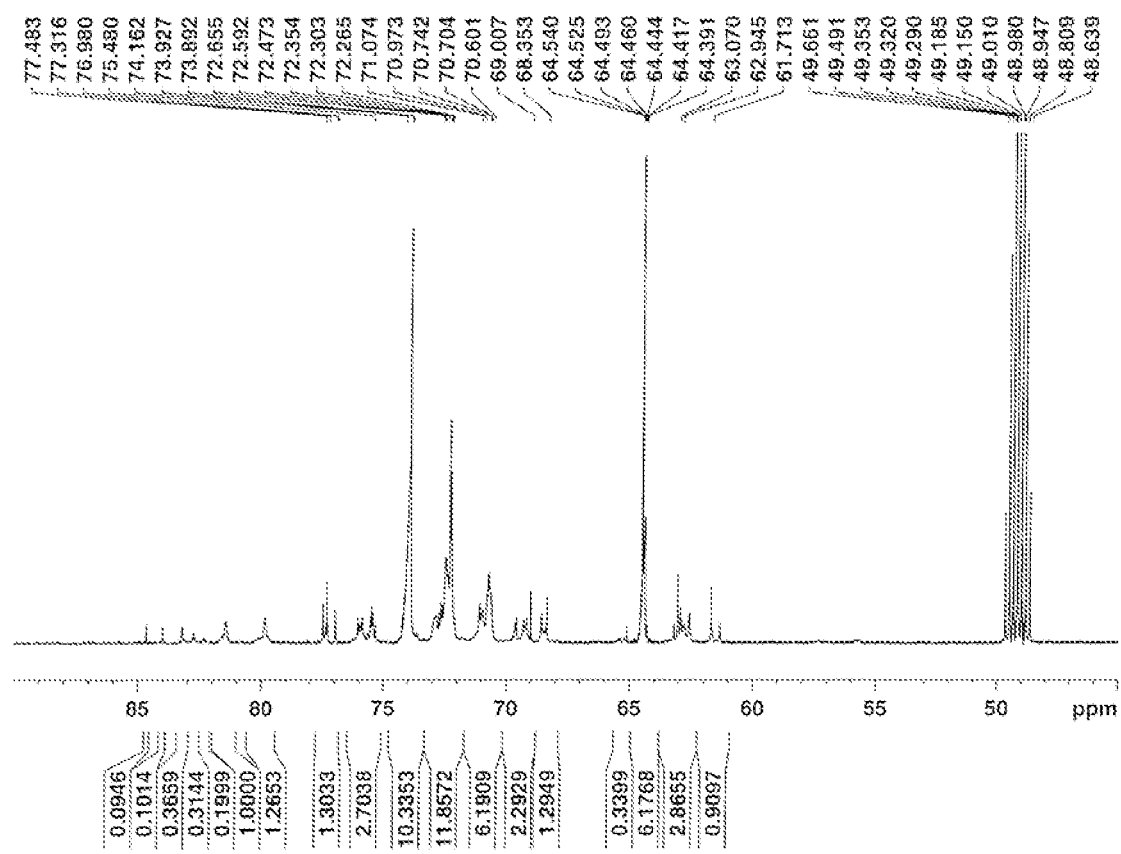

BRANCHED POLYMERIC EMULSIFIERS

CROSS REFERENCE TO RELATED APPLICATION

This application claims priority from PCT application Ser. No. PCT/US2013/054103 filed on Aug. 8,2013, which claims the benefit of U.S. Provisional Application No. 61/692,303 filed on Aug. 23,2012.

FIELD OF THE INVENTION

The present invention relates to esterified glycerylated alkyl glycosides and to a process for making same. These compounds are useful as emulsifiers and coemulsifiers in the formulation of phase stable emulsions suitable for use in personal care, home care, industrial and institutional, and health care applications.

BACKGROUND OF THE INVENTION

A wide variety of personal care and cosmetic products are essentially oil-in-water (O/W) emulsions, comprising finely divided oil droplets dispersed homogeneously in an aqueous solution. The commonly used oils or oil like substances range from various esters and triglycerides to various hydrocarbons and silicone fluids. These emulsions may contain high levels of active benefit agents intended to deliver skin care, hair care, and other benefits. Many of these agents are electrolytic and/or acidic compounds which pose considerable challenges towards maintaining good stability of the emulsions during their storage. Stabilizing these emulsions against separation of the oil phase (coalescence) or agglomeration (flocculation) of emulsion droplets, when the emulsions contain high levels of electrolytes, and/or have an extreme pH, would require the use of a highly effective emulsifier.

Surface active polymers (or polymeric surfactants) that are capable of adsorbing at an oil/water interface typically perform more efficiently than low molecular weight surfactants, as an emulsifier. Generally, once polymers adsorb onto and thus coat the surface of emulsion droplets, they can provide for a strong, long range droplet-to-droplet repulsion, known as steric repulsion in the art, which in turn prevents the emulsion droplets from closely approaching one another, in effect, stabilizing the droplets against flocculation and coalescence.

Synthetic and semi natural polymeric emulsifiers are widely used in overcoming the aforementioned challenges in formulating stable emulsions for personal care and cosmetic products. A vast majority of the synthetic polymeric emulsifiers in use today are esterified polyethoxylated polymers, an example of which is PEG-100 stearate. The semi natural polymeric emulsifiers are derived from naturally occurring polyols, such as sugars, glycerides and saccharides, which are subsequently modified by ethoxylation and/or lipophilic esterification, e.g., ethoxylated methyl glucose esterified with a fatty acid. However, a serious health concern surrounds these PEG containing ingredients, ever since it became known that ethoxylated materials can generate the highly toxic substance, 1,4-dioxane, in their manufacture.

Oil-in-water (O/W) emulsions formulated into personal care and cosmetic products typically contain polymeric thickening agents in the water phase of the emulsion. When a polymeric surfactant is used as an emulsifier, an amount of the polymer adsorbs onto the surface of the emulsion droplet, while the rest (free or unadsorbed) remains dissolved in the water phase, maintaining a thermodynamic equilibrium between the adsorbed and free polymer. The higher the concentration of the polymer, the higher the amount of the free polymer that is present in the solution phase. The polymeric emulsifier possibly can interact with the polymeric thickening agent, for example, via hydrogen bonding and/or hydrophobic interactions, such interpolymer interactions in some cases could potentially reduce the efficacy of the thickening agent.

A way to avoid the foregoing problem is to formulate emulsions that have relatively large sized droplets, while maintaining good emulsion stability. It is, however, generally more difficult to stabilize large emulsion droplets against flocculation because the larger the emulsion droplet, the stronger the van der Waals attraction acting between them. This ubiquitous inter-droplet attraction tends to oppose any inter droplet repulsion instilled, for example, through the use of a polymeric emulsifier. For a given weight of an emulsified oil phase, larger emulsion droplets would present a lower total (interfacial) surface area to be coated by the emulsifier. Accordingly, the larger the size of an emulsion droplet, a lower emulsifier dosage may be required for effecting good emulsion stability ameliorating any adverse effects of an emulsifier/thickener interaction.

Furthermore, it is often desirable in the manufacturing of personal care products that highly concentrated O/W emulsions are produced first in stable and pumpable (i.e., not overly viscous) forms, which can be stored for a period of time (generally as long as several days or weeks) before they are diluted with additional ingredients for producing the final product. Clearly, it is critical that such concentrated emulsions remain stable against flocculation and coalescence, and retain a pumpable consistency during and after the storage period.

It is often challenging to produce stable O/W emulsions, if the amount of the oil phase exceeds 55 to 60 wt. % of the emulsion. Also, even when free of any thickening agent, O/W emulsions can be highly viscous if the emulsion droplets undergo extensive flocculation (wherein an amount of the water phase gets entrapped within the flocs and is no longer available to impart fluidity to the emulsion). Furthermore, in concentrated emulsions, the smaller and the more uniform the size of the emulsion droplets, the higher is the emulsion viscosity. Hence, a way to provide highly concentrated yet low viscosity emulsions is to produce emulsions with a relatively large droplet size, while ensuring that the droplets are substantially stable against flocculation.

The recent consumer demand for personal care products to be derived from naturally sourced ingredients, given that their use involves bodily contact have led product formulators to include vegetable oils as the oil phase component in O/W emulsions. However, emulsifying these oils, which are primarily composed of triglycerides, into stable emulsions is challenging. The aforementioned polyethoxylated emulsifiers are very effective emulsifiers for these oils. While the semi natural emulsifiers include naturally sourced components, they are increasingly seen as less sustainable because of the use of petrochemically derived ethylene oxide in their manufacture. Moreover, because of the health and safety concerns associated with ethoxylated materials, there is a growing need for ethoxylate free emulsifiers that provide efficient and stable emulsification of oil phase components, particularly when vegetable oils are utilized as the oil phase.

For the foregoing reasons, it would be beneficial to provide an emulsifier that is substantially derived from naturally sourced materials and free of toxic contaminants for use in products formulated as O/W emulsions. It also would be beneficial to deliver an emulsifier with the properties described above, that could be successfully used in stabilizing O/W emulsions of natural oils such as vegetable derived oils.

To the best of our knowledge, such a desirable emulsifier for O/W emulsions (particularly in personal care and cosmetic product emulsions) has not been disclosed in the art. Accordingly, there is a need for an emulsifier that meets the foregoing parameters.

SUMMARY OF THE INVENTION

In one aspect, embodiments of the present invention relate to an emulsifier that is polymeric in nature, is capable of stabilizing highly concentrated (with respect to the oil phase) O/W emulsions in the presence of high levels of an electrolyte over a wide pH range, and is free of any ethylene oxide (EO) residue groups. The emulsifier is capable of producing low viscosity emulsions even when the concentration of the oil phase is relatively high. The emulsifier is additionally capable of stabilizing relatively large sized emulsion droplets, even in highly concentrated emulsions, which in turn enables a lower emulsifier concentration requirement (thus keeping any undesirable interactions between the emulsifier and polymeric thickening agent at a minimum), as well as producing highly concentrated, yet, low viscosity emulsions.

These and other aspects of the invention are provided by an esterified polyglyceryl alkyl glycoside polymer. The polymer comprises an alkyl glycoside core moiety with branched polyglyceryl ether chains radiating therefrom, wherein the sum of the glyceryl residues present on the polymer range from about 20 to 150, and wherein at least a portion of the polyglyceryl chains contain an acyl moiety containing 8 to 54 carbon atoms.

BRIEF DESCRIPTION OF THE DRAWINGS

FIG. 1 is a $^{13}$C-NMR spectrum at 125.77 MHz of the polyglycerylated methyl glucoside prepared in Example 16.

DESCRIPTION OF EXEMPLARY EMBODIMENTS

Exemplary embodiments in accordance with the present invention will be described. Various modifications, adaptations or variations of the exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

While overlapping weight ranges for the various components and ingredients that are contemplated in the compositions of the invention have been expressed for selected embodiments and aspects of the invention, it should be readily apparent that the specific amount of each component in the disclosed compositions will be selected from its disclosed range such that the amount of each component is adjusted such that the sum of all components in the composition will total 100 wt. %. The amounts employed will vary with the purpose and character of the desired product and can be readily determined by one skilled in the art.

Unless otherwise stated, all percentages, parts, and ratios expressed herein are based upon weight of the total compositions of the present invention.

The polymers and compositions of the present invention may suitably comprise, consist of, or consist essentially of the components, elements, and process delineations described herein. The invention illustratively disclosed herein suitably may be practiced in the absence of any element which is not specifically disclosed herein.

The term "personal care" as used herein includes, without being limited thereto, cosmetics, toiletries, cosmeceuticals, beauty aids, insect repellents, personal hygiene and cleansing products applied to the body, including the skin, hair, scalp, and nails of humans and animals.

The term "home care products" as used herein includes, without being limited thereto, products employed in a domestic household for surface cleaning or maintaining sanitary conditions, such as in the kitchen and bathroom (e.g., hard surface cleaners, hand and automatic dish care, toilet bowl cleaners and disinfectants), and laundry products for fabric care and cleaning (e.g., detergents, fabric conditioners, pretreatment stain removers), and the like.

The term "health care" as used herein includes, without being limited thereto, pharmaceuticals (controlled release pharmaceuticals), pharmacosmetics, oral care (mouth and teeth) products, such as oral suspensions, mouthwashes, toothpastes, dentifrices, and the like, and over the counter products and appliances (topical and transdermal), such as patches, plasters and the like, externally applied to the body, including the skin, scalp, nails and mucous membranes of humans and animals, for ameliorating a health-related or medical condition, for generally maintaining hygiene or well-being, and the like.

The term "institutional and industrial care" ("I&I") as used herein includes, without being limited thereto, products employed for surface cleaning or maintaining sanitary conditions in institutional and industrial environments, textile treatments (e.g., textile conditioners, carpet and upholstery cleaners), automobile care (e.g., hand and automatic car wash detergents, tire shines, leather conditioners, liquid car polishes, plastic polishes and conditioners), paints and coatings, and the like.

The term "glycoside" as used herein includes the acetal formed by the reaction of an alcohol with a carbonyl group of a monosaccharide, disaccharide, or oligosaccharide containing 3 to 10 saccharide residues. The monosaccharides include, but are not limited to, glucose, fructose, mannose, arabinose, gulose, xylose, lyxose, erythrose, threose, galactose, and sorbose. The disaccharides include, but are not limited to, maltose, lactose, cellobiose and sucrose. The glycoside derived from glucose is termed a "glucoside".

The term "alkyl glycoside" as used herein means a glycoside molecule that has one alkyl group attached through a hemiacetal, bond wherein the alkyl group contains 1 to 22 carbon atoms. Alkyl glycosides may be prepared by the condensation reaction of glucose with an alcohol in the presence of an acid catalyst. For example, methyl glucoside can be prepared by the reaction of glucose with methanol, and decyl glucoside can be prepared by the reaction of glucose with decyl alcohol. An alkyl glycoside having two or more linked glucosidic repeating units is termed an "alkyl polyglucoside".

The term "glycerylated alkyl glycoside" as used herein means the reaction product of an alkyl glyceride (e.g., alkyl glucoside) with a glycerylation agent such as glycerol (IUPAC: propane-1,2,3-triol), α-glycerol chlorohydrin (IUPAC: 3-chloropropane-1,2-diol), glycidol (IUPAC: oxiranylmethanol) or glycerine carbonate (IUPAC: 4-hydroxymethyl-1,3-dioxolan-2-one).

The term "glyceryl unit" or "glyceryl residue" as used herein means the residue formed from the reaction of a glycerylation agent disclosed above with a hydroxyl group to form an ether linkage. Examples of glyceryl structural units are as follows:

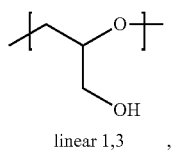

linear 1,3 ,

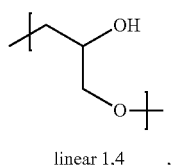

linear 1,4 ,

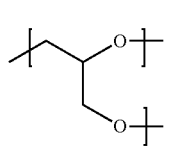

branched ,

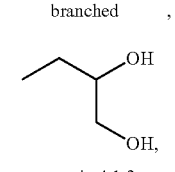

terminal 1,2

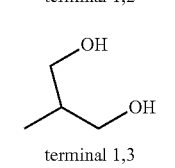

terminal 1,3

Additionally, the following glyceryl unit structures are theoretically possible:

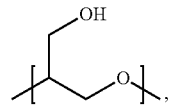

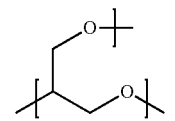

The term "polyglyceryl" as used herein means that 2 or more glyceryl units are linked together via ether linkages formed from the reaction primary and/or secondary in the same chain.

The term "ether linkage" as used herein also includes the ether bond formed through the reaction of the glycerylation agents disclosed above with a hydroxyl group situated on the alkyl glycoside. When two or more glyceryl units are present in a polyglyceryl chain, the chain can be linear or branched.

The term "esterified glycerylated alkyl glycosides" as used herein means a glycerylated alkyl glycoside that has been esterified with a $C_8$-$C_{54}$ fatty acid.

The esterified polyglyceryl alkyl glycoside and alkyl polyglucoside of the invention is a highly branched polymer comprising linear and branched polyglyceryl chains, wherein the average degree of glyceryl polymerization ranges from about 20 to about 150 in one aspect, from about 30 to about 140 in second aspect, from about 40 to about 130 in a third aspect, from about 50 to 120 in a fourth aspect, from about 60 to about 115 in a fifth aspect, and from about 65 to about 110 in a sixth aspect. The average degree of glyceryl polymerization means the total moles of glyceryl repeat units present per mole of the alkyl glycoside or alkyl polyglucoside on a number average basis. The polymer core comprises an alkyl glycoside core or alkyl polyglucoside core unit with esterified polyglyceryl arms emanating from the core. In one aspect, the core is derived from a monosaccharide, a disaccharide, or an oligosaccharide containing from about 2 to 10 saccharide residues.

In one aspect of the invention, the esterified polyglyceryl alkyl glycoside emulsifier of the invention comprises an alkyl glucoside core with esterified linear and/or branched polyglyceryl chains attached to the core. The alkyl glucoside core is highly branched in that the esterified linear and/or branched polyglyceryl chains radiate from the core in a star polymer like morphology. The esterified glycerylated alkyl glucoside can be represented by structural formula (I):

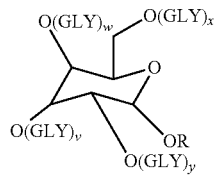

wherein R represents an alkyl group containing 1 to 22 carbon atoms; GLY is a substituted or unsubstituted glyceryl or polyglyceryl moiety or residue represented by the formulae:

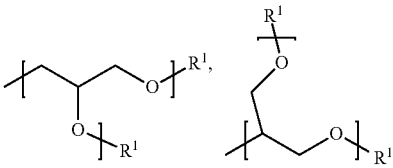

and combinations thereof, wherein $R^1$ can be the same or different and is selected from hydrogen, an acyl group containing 8 to 54 carbon atoms, and GLY, wherein GLY is as defined above, the sum of v+w+x+y is an integer ranging from about 20 to about 150, subject to the proviso that a portion of $R^1$ represents said acyl group.

In one aspect, the average degree of glyceryl polymerization, i.e., the total moles of glyceryl units present on the alkyl glycoside (the sum of v+w+x+y), ranges from about 20 to about 150 in one aspect, from about 30 to about 140 in second aspect, from about 40 to about 130 in a third aspect, from about 50 to 120 in a fourth aspect, from about 60 to about 115 in a fifth aspect, and from about 65 to about 110 in a sixth aspect, any one of v, w, x, and y can be 0, subject to the proviso that they cannot all be 0 at the same time.

In one aspect, the average degree of glyceryl polymerization, i.e., the total moles of glyceryl units present on the alkyl glycoside (the sum of v+w+x+y), ranges from about 20 to about 150 in one aspect, from about 30 to about 140 in second aspect, from about 40 to about 130 in a third aspect, from about 50 to 120 in a fourth aspect, from about 60 to about 115 in a fifth aspect, and from about 65 to about 110 in a sixth aspect, any one of v, w, x, and y can be 0, subject to the proviso that they cannot all be 0 at the same time, and when any of v, w, x, or y is 0, $R^1$ cannot represent an acyl moiety.

Emulsifier Preparation

The esterified glycerylated alkyl glycosides of the invention are prepared by the reaction of an un-esterified alkyl glycoside compound (i.e., an alkyl glycoside devoid of acyl moieties) with a glycerylation agent such as glycerol, chloroglycerin (α-glycerol chlorohydrin), glycidol or glycerine carbonate to give a linear and/or branched glycerylated alkyl glycoside intermediate. This intermediate is subsequently reacted with a $C_8$-$C_{54}$ fatty acid to yield the esterified linear and/or branched glycerylated alkyl glycoside emulsifier. The fatty acid reacts with a portion of the primary and/or secondary hydroxyl groups on the polyglyceryl modified alkyl glycoside to yield the esterified glycerylated alkyl glycoside emulsifiers of the invention.

In one aspect of the invention, the alkyl glycoside employed as the base starting material for the glycerylation reaction is an alkyl glucoside or an alkyl polyglucoside wherein the alkyl group contains 1 to 22 carbon atoms in one aspect, 1 to 18 carbon atoms in another aspect, 1 to 16 carbon atoms in still another aspect, 1 to 12 carbon atoms in a further aspect, 1 to 10 carbon atoms in a still further aspect, and 1 to 5 carbon atoms in another aspect. Alkyl glucosides and alkyl polyglucoside (APG) base materials of the invention can be represented by the structural formulas IB and IIB, respectively, as follows.

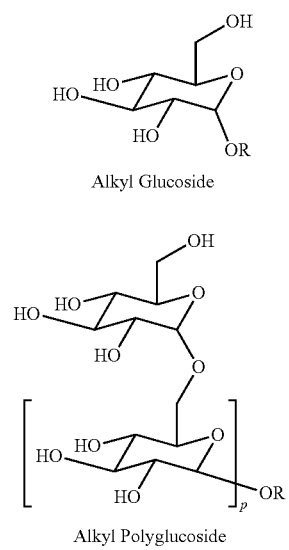

Alkyl Glucoside

Alkyl Polyglucoside wherein R is an alkyl group containing 1 to 22 carbon atoms and p ranges from 0 to 9 in one aspect and from 1 to 9 in another aspect. When p is 0, the structure represents an alkyl glucoside of formula IB, and when p is 1 to 9, the structure represents an alkyl polyglucoside of formula IIB. The degree of oligomerization, p, represents a mean value from the distribution of monoglucosides and polyglucosides. As a calculated quantity, the degree of oligomerization is representative of the distribution of the chemical individuals present in a given oligomer mixture which differ from one another in the number of glucose residues present per alkyl glucoside molecule. The average degree of oligomerization, p, is a value ranging from about 0 or 1 to about 3 in one aspect, from about 1.1 to about 2.5 in another aspect, from about 1.2 to about 2.1 in still another aspect, and from about 1.3 to about 1.6 in a further aspect. Alkyl glucosides and alkyl polyglucosides are well-known in the art and are readily available in the commercial trade.

In certain aspects, the alkyl glucoside utilized as the base glucoside for the glycerylation reaction is methyl glucoside, ethyl glucoside, propyl glucoside, butyl glucoside, and amyl glucoside which are devoid of any acyl moieties. In one aspect, the alkyl glucoside is methyl glucoside (MeG) wherein R in formula IB is a methyl group and no acyl substitution is present on the methyl glucoside core.

In one aspect of the invention, glycerylation entails reacting the pendant hydroxyl groups present on the alkyl glucoside or alkyl polyglucoside with the above disclosed glycerylation agents to give a glycerylated intermediate product. In another aspect of the invention, glycerylation entails reacting all of the pendant hydroxyl groups present on the alkyl glucoside or alkyl polyglucoside with the above disclosed glycerylation agents to give a glycerylated intermediate product. The glycerylation agent reacts with a pendant hydroxyl group(s) on the alkyl glucoside or alkyl polyglucoside to form a glyceryl and/or polyglyceryl units attached to the alkyl glucoside or alkyl polyglucoside through an ether linkage. Unlike the linear structures of polyethoxylated methyl glucoside, the polyglyceryl MeG derivatives of the present invention are hyperbranched or dendrimer like. A dendrimer is generally described as a macromolecule with the characteristically tree like, highly branched 3 dimensional globular architecture that provides a high degree of surface functionality and versatility. Dendrimers can be considered to consist of 3 major portions: a core, an inner shell, and an outer shell. Theoretically, assuming that each of the 4 hydroxyl groups on the MeG core (generation 0) react with the glycerylation agent to give polyglyceryl-4 methyl glucoside (generation 1), and all primary and secondary hydroxyl groups present on each of the four glyceryl units (i.e., 8 hydroxyl groups) of polyglyceryl-4 methyl glucoside participate in a subsequent reaction cycle with the glycerylation agent (generation 2) it is readily apparent that the number of glyceryl units with potentially reactive hydroxyl groups attached to the MeG core increase exponentially with each succeeding generation (e.g., generation 1, 2, 3, . . . n) as illustrated in the table below.

| Generation | No. of Glyceryl Units of Outer Shell | No. of Terminal Hydroxyl Groups | Total No. of Glycerine Units | Molecular Weight |
|---|---|---|---|---|
| 0[1] | 0 | 4 | 0 | 194 |
| 1 | 4 | 8 | 4 | 490 |
| 2 | 8 | 16 | 4 + 8 | 1982 |
| 3 | 16 | 32 | 4 + 8 + 16 | 2266 |
| 4 | 32 | 64 | 4 + 8 + 16 + 32 | 4634 |
| 5 | 64 | 128 | 4 + 8 + 16 + 32 + 64 | 9370 |
| n | $2^{(n+1)}$ | $2^{(n+2)}$ | $4(2^n - 1)$ | $194 + 74 * 4(2^n - 1)$ |

[1]MeG Core prior to glycerylation

While the theoretical dendrimeric structure is illustrated above, it is readily apparent that in practice a theoretical structure would rarely be obtained due to the relative reactivities of the primary and secondary hydroxyl groups in each glyceryl unit. Moreover, steric hindrance may also play a part in deviating from the theoretical dendrimeric structure. In one aspect of the invention, the products obtained by the base catalyzed living anionic polymerization of a glycerylation agent (e.g., glycidol, glycerine carbonate) with an alkyl glucoside (e.g., methylglucoside) yields a combination of linear, branched and/or hyperbranched polyglyceryl moieties situated on the alkyl glucoside or alkyl polyglucoside core.

Linear polyglyceryl moieties are defined to mean that the glyceryl units are joined to one another to create a linear chain. Branched polyglyceryl moieties are defined to mean that the polyglyceryl chain contains at least one branch point where a second chain of glyceryl units branches off from the first chain. Hyperbranched polyglyceryl moieties are defined to mean that the polyglyceryl chain contains multiple branch points, for example, where a second chain of glyceryl units branches off from the first chain and a third polyglyceryl chain branches off from the second chain, and so on.

The polyglyceryl alkyl glucosides and alkyl polyglucosides (e.g., MeGs and APGs) and their ester derivatives prepared in accordance with the present invention are branched and/or hyperbranched) meaning that a portion of the polyglyceryl chains attached to the alkyl glucoside or alkyl polyglucoside core of the invention contain branched glyceryl structural units as confirmed by $^{13}$C-NMR.

To prepare the emulsifiers of the present invention, various synthesis routes can be utilized. In one aspect, the alkyl glucoside or alkyl polyglucoside is reacted with a glycerylation agent such as glycidol or glycerine carbonate via based catalyzed ring-opening living anionic polymerization to obtain the polyglycerylated intermediate. Suitable base catalysts include, but are not limited to, alkali metal hydroxides (e.g., NaOH, KOH), alkali metal carbonates and bicarbonates (e.g., $K_2CO_3$, $Na_2CO_3$, $KHCO_3$, $NaHCO_3$), and sodium or potassium $C_1$-$C_4$ alkoxides (e.g., sodium methoxide, potassium methoxide). The base catalyst, particularly the alkali metal hydroxides, can be buffered with a polybasic acid, such as a phosphorus oxyacid (e.g., hypophosphorous acid, phosphorus acid, phosphoric acid). The amount of base utilized in the preparation of the glycerylated alkyl glucoside or alkyl polyglucoside ranges from about 0.2 to about 0.5 wt. % based on the total weight of the reaction medium and the glycerylation agent. The amount of buffer or antioxidant if utilized can range from about 0.1 to 0.5 wt. % of the total reaction medium. The catalyst facilitates the formation of alkyl glucoside and alkyl polyglucoside metal alkoxide initiator species by the replacement of the hydroxyl hydrogen(s) with a metal.

The synthesis reaction will generally be carried out in a one pot semi batch process (wherein the glycerylation agent (monomer) and/or catalyst are added occasionally at multiple intervals during the reaction); although a batch process (wherein all reactants are added to the reaction vessel at one time, mixed and allowed to react) can be used. It is also possible to employ continuous or semi continuous processes if desired.

Typically, the reactions to make the compounds of the invention can be carried out without the need for a solvent or diluent, particularly as this will avoid any problem in isolating the desired product. However, if desired, the physical immiscibility of the starting materials may be avoided by the use of suitable inert reaction medium, solvent or diluent; however, the reaction is preferably conducted in the bulk. Suitable solvents are liquids which remain thermally stable and are inert to the reagents and products. Any solvent used will either have a relatively low vapor pressure at the reaction temperature or the reaction will be conducted under suitable containment or reflux arrangements. Suitable examples of solvents/diluents include dimethyl isosorbide, dimethylformamide, dimethylsulfoxide, and ethylene glycol diethers and diethylene glycol diethers, e.g., dimethyl, diethyl, dibutyl ethers.

The reaction temperature can range from at least 100° C. up to about 220° C. in one aspect, from about 120 to about 200° C. in another aspect, from about 150 to about 190° C. in still another aspect and from about 160 to about 180° C. in a further aspect. In one aspect, due to the ketal sensitivity of the alkyl glucoside and alkyl polyglucoside to high temperatures, the reaction temperatures ideally are below 200° C.

Typically, the reagents used to make the compounds of the invention remain liquids of low vapor pressure at reaction temperatures, so that the reaction can be conveniently carried out at ambient pressure though lower and higher pressures may be used if desired.

In one aspect, it is desirable to apply a vacuum to the reaction medium initiator during initial heating to degas and dry the initiator, as entrained oxygen may lead to discoloration of the product, and entrained water can lead to spontaneous initiation of the subsequently added glycerylation agent, resulting in competing side reactions. In another aspect, it may also be desirable to apply a vacuum to the monomers prior to the reaction for degassing and drying purposes. To help avoid excessive color generation, the synthesis reactions can usually be carried out in a largely oxygen free atmosphere, e.g. in a nitrogen atmosphere (e.g., using a nitrogen blanket or sparge).

It may be desirable to include an antioxidant in the reaction medium to aid in control of product color. Reducing agents commonly used for this purpose, particularly in the manufacture of personal care products, can be used in this invention and examples include phosphorus acid, hypophosphorous acid, and borohydride (usually as sodium borohydride). Where the reducing agent is itself an acid, e.g., phosphorus or hypophosphorous acid, it will usually be present as a salt, typically an alkali metal salt. The salt may be made in situ by reaction with base, e.g., part of the basic catalyst (where used) and in this case care may be needed to ensure that sufficient base is present to neutralize the reducing acid and to act as catalyst. When used, the amount of reducing agent will typically be from about 0.1 to about 0.5 wt. %, based on the weight of the alkyl glucoside/alkyl polyglucoside and glycerylation agent in the reaction medium.

In one aspect, the molar ratio of initiator to glycerylation agent used in the synthesis is 1:50 to 1:120 in one aspect, from about 1:60 to 1:115 in another aspect, from about 1:65 to 1:110 in still another aspect, and from about 1:4 in a further aspect. For higher degree of polymerization values more glycerylation agent and/or catalyst may be metered into the reaction medium as the concentration of glycerylation agent diminishes.

The propagation of the polyglyceryl chains is conducted by the addition of the glycerylation agent into the reaction medium in a controlled semi batch manner so that the molecular weight of the polymer can be controlled by the molar ratio of monomer to initiator so that side reactions involving the homopolymerization of free polyglyceryl moieties (i.e., polyglyceryl moieties not attached to the alkyl glucoside or alkyl polyglucoside core) is minimized. Generally, the more monomer that is present in the reaction system the more likely such side polymerizations are to occur and consequently, aliquot or gradual addition of monomers over the course of the reaction reduces the amount of side product made.

For the synthesis route employing glycidol, the reaction temperature ranges from about 100 to about 140° C. in one aspect, from 100 to 130° C. in another aspect, and from about 100 to 120° C. in a further aspect. The rate of addition of glycidol into the reaction medium is controlled such that a 2 to 4 fold amount by weight of glycidol is added per hour based on the dry weight of the alkyl glucoside or alkyl polyglucoside. To determine the presence or absence of glycidol in the reaction mix as the reaction proceeds to completion, the reaction mix can be periodically sampled and analyzed by infrared spectrometry to determine the presence or absence of the IR peak at 916 cm$^{-1}$ characteristic of glycidol.

For the synthesis route employing glycerine carbonate, the reaction temperature ranges from about 140 to about 200° C. in one aspect, from about 150 to about 190° C. in another aspect, and from about 160 to about 180° C. in a further aspect. The rate of addition of glycerine carbonate into the reaction medium is controlled such that a 3 to 5 fold amount by weight of glycerine carbonate is added per hour based on the dry weight of the alkyl glucoside or alkyl polyglucoside. To determine the presence or absence of glycerine carbonate in the reaction mix as the reaction proceeds to completion, the reaction mix can be periodically sampled and analyzed by infrared spectrometry to determine the presence or absence of the IR peak at 1790 cm$^{-1}$ characteristic of glycerine carbonate.

The alkyl glucoside core material (generation 0) has 4 hydroxyl groups available for reaction with the glycerylation agents of the invention. Theoretically all or a portion of these hydroxyl groups can be derivatized (glycerylated) in accordance with the invention. The total degree of glyceryl substitution ($DS_g$) is 1.0 when one hydroxyl group is derivatized, 2.0 when on average 2 hydroxyl groups are derivatized, 3.0 when on average 3 hydroxyl groups are derivatized, and 4.0 when on average 4 hydroxyl groups are derivatized in a given composition. The average total $DS_g$ values can be shown as decimal fractions of these integer values, and mean that the alkyl glucoside composition comprises alkyl glucoside molecules having whole number $DS_g$ values embracing the average. The average $DS_g$ for the alkyl glucoside of the invention ranges from about 1 to about 4 in one aspect, from about 2 to about 4 in another aspect, and about 3 to about 4 in a further aspect. In another embodiment, the total $DS_g$ for the glycerylated alkyl glucosides of the invention range from about 1.5 to about 3.75 in one aspect, from about 1.8 to about 3.5 in another aspect, from about 2.25 to about 3.25 in a further aspect. The average amount of polyglyceryl substitution ($DS_g$) per mole of alkyl glucoside can be determined by any technique known to those skilled in the art, e.g., by nuclear magnetic resonance spectroscopy (NMR).

As can readily be determined from formula IIB, the alkyl polyglucosides of the invention have a minimum of 7 available hydroxyl groups when p=1 (i.e., 4 hydroxyl groups contributed by the terminal glucosidic residue and 3 hydroxyl groups contributed by the succeeding glucosidic residue). For every successive glucosidic residue in the oligomeric chain, 3 additional hydroxyl groups are available for glycerylation. When p=9, the total number of hydroxyl groups that are available for reaction is 31 (including 4 hydroxyl groups contributed by the terminal alkyl glucosidic residue). The average degree of glyceryl substitution ($DS_g$) for the alkyl polyglucoside of the invention is calculated on the basis of the available hydroxyl groups per glucosidic residue. As described previously, the terminal glucosidic residue of the alkyl polyglucoside has a maximum hydroxyl content of 4, while each succeeding glucosidic residue has a maximum hydroxyl content of 3. Taking into account that the terminal glucosidic residue of the alkyl polyglucoside contains 4 hydroxyl groups, the average total (maximum) $DS_g$ values per glucosidic residue across the entire oligomer can be calculated by adding the total number of hydroxyl groups and dividing this total by the number of glucosidic residues present. Average total DS values are shown as decimal fractions of these integer values, and mean that the alkyl polyglucoside is made up of glycoside units having whole number DS values embracing the average. The following table summarizes the hydroxyl content of the alkyl polyglucoside core material.

| T + (p)[1] | No. of Repeating Units | Total No. of OH Groups | Average Total No. of OH Groups/Residue |
|---|---|---|---|
| T + 1 | 2 | 7 | 3.5 |
| T + 2 | 3 | 10 | 3.33 |
| T + 3 | 4 | 13 | 3.25 |
| T + 4 | 5 | 16 | 3.2 |
| T + 5 | 6 | 19 | 3.16 |
| T + 6 | 7 | 22 | 3.14 |
| T + 7 | 8 | 25 | 3.13 |
| T + 8 | 9 | 28 | 3.11 |
| T + 9 | 10 | 31 | 3.1 |

[1]Terminal (T) glucosidic residue + succeeding glucosidic residue (p)

The average $DS_g$ (per glucosidic residue) for the alkyl polyglucoside of the invention ranges from about 1 to about 3.5 in one aspect, from about 1.5 to about 3.25 in another aspect, from about 1.8 to about 2.5 in still another aspect, and from about 2.8 to about 3 in a further aspect.

Suitable acylating reagents for esterifying the polyglycerylated alkyl glucoside and polyglycerylated alkyl polyglucoside intermediates of the invention are selected from $C_8$ to $C_{54}$ fatty acids and ester derivatives thereof. These reagents typically provide an ester linkage through a hydroxyl group situated on a polyglyceryl chain attached to the alkyl glucoside and alkyl polyglucoside.

Esterification is effected with an acylating agent. The acylation agent can be naturally or synthetically derived. Suitable fatty acid acylating agents include, but are not limited to, those which are typically obtained by hydrolyzing vegetable oils and animal oils such as coconut oil, palm oil, tallow, fish oil, linseed oil, rape seed oil, sunflower seed oil, peanut oil, safflower oil, soybean oil, castor oil, tall oil, and the like. Fatty acids obtained from microorganisms can also be used to effect esterification.

Exemplary fatty acids include, but are not limited to, caprylic acid, pelargonic acid, capric acid, undecanoic acid, lauric acid, myristic acid, palmitic acid, palmitoleic acid, stearic acid, isostearic acid, oleic acid, ricinoleic acid (12-hydroxy-9-cis-octadecenoic acid), vaccenic acid, linolenic acid, α-linolenic acid, γ-linolenic acid, arachidic acid, gadoleic acid, arachidonic acid, eicosapentaenoic acid (EPA), behenic acid, docosahexaenoic acid (DHA), lignoceric acid, and mixtures thereof.

Synthetically derived dimer and trimer acids containing 36 to 54 carbon atoms are also suitable acylating agents. Processes for forming these acids are well-known and are disclosed in numerous U.S. Pat. Nos. including 2,482,761, 2,793,220, 2,793,221 and 2,955,121. In carrying the dimer and trimer synthesis, unsaturated fatty monomer acids such as oleic, linoleic, linolenic acid, ricinoleic acid or mixtures of such acids (all of essentially $C_{18}$ chain length) are heated in the presence of water, or in the presence of both water and an active clay mineral, to induce polymerization (dimerization, trimerization). The polymeric fatty acid reaction mixtures so prepared contain from about 30 to 75 wt % of the acid polymer, with the balance of the mixture representing $C_{18}$ monocarboxylic monomer acids of one type or another which can be separated from the mixture once the polymerization operation is concluded. The residual polymer fraction consists essentially of dimer ($C_{36}$ acids) together with amounts up to about 20 to about 22 wt. % of trimer ($C_{54}$ acids). The dimer and trimer acids can be separated, if desired, by conventional means known in the art such as, for example, distillation. These polymerization reaction products can be used in the form in which they are recovered from the polymerization unit, or they can be given a partial or complete hydrogenation treatment to reduce unsaturation before being reacted with the polyglycerylated intermediates of the invention. Dimer acids are also commercially available such as, for example, Pripol™ dimerized fatty acids from Croda.

The esterification can be effected by the direct acylation of the polyglycerylated intermediates of the invention with a fatty acid or mixtures of fatty acids or through an ester exchange (transesterification) reaction between the polyglycerylated intermediates with lower alkyl esters having 1 to 8 carbon atoms such as the methyl, ethyl and propyl esters of the fatty acids described above, as well as mixtures thereof.

The amount of acylating agent used to derivatize the polyglyceryl alkyl glucoside intermediate of the invention is chosen to effectively promote stable emulsification of the discontinuous phase in a two phase O/W system. The emulsifiers are prepared by acylating the polyglycerylated alkyl glucoside and polyglyceryl alkyl polyglucoside intermediates with from about 1 to about 4 moles of the acylating agent per mole of polyglycerylated alkyl glucoside intermediate. The average degree of acyl substitution ($DS_a$) for the glycerated alkyl glucoside of the invention ranges from about 1 to about 4 in one aspect, from about 2 to about 4 in another aspect, and about 3 to about 4 in a further aspect. Average $DS_a$ values can be shown as decimal fractions of these integer values, and mean that the alkyl glucoside composition comprises alkyl glucoside molecules having whole number $DS_a$ values embracing the average. In another embodiment, the average $DS_a$ for the glycerylated alkyl glucosides of the invention range from about 1.8 to about 3.75 in one aspect, from about 1.8 to about 3.5 in another aspect, from about 2.25 to about 3.25 in a further aspect. The average amount of polyglyceryl substitution ($DS_a$) per mole of alkyl glucoside can be determined by any technique known to those skilled in the art, e.g., by NMR.

The average $DS_a$ (per glucosidic residue) for the glycerylated alkyl polyglucoside of the invention ranges from about 1 to about 3.5 in one aspect, from about 1.5 to about 3.25 in another aspect, from about 1.8 to about 2.5 in still another aspect, and from about 2.8 to about 3 in a further aspect. Average total $DS_a$ values are shown as decimal fractions of these integer values, and mean that the glycerylated alkyl polyglucoside is made up of glycoside units having whole number $DS_a$ values embracing the average.

The esterification reaction can typically be conducted in the same reactor (one pot synthesis) immediately following the glycerylation of the alkyl glucoside or alkyl polyglucoside. In one aspect, the glycerylated alkyl glucoside or glycerylated alkyl polyglucoside is acylated by transesterification with a lower alkyl ester of a desired fatty acid in the optional presence of a base catalyst. The catalyst can be selected from the same sodium or potassium $C_1$-$C_4$ alkoxides (e.g., sodium methoxide, potassium methoxide) utilized in the glycerylation of the alkyl glucoside and alkyl polyglucoside.

The reaction mixture containing the glycerylated alkyl glucoside or glycerated alkyl polyglucoside, lower alkyl ester of the desired fatty acid, and the base catalyst is heated to a reaction temperature ranging from about 130 to about 200° C. in one aspect, from about 140 to about 185° C. in another aspect, and from 160 to about 170° C. in a further aspect. Generally from about 0.01 to about 0.50 wt. % in one aspect, from about 0.03 to 0.2 wt. % in another aspect, and from about 0.05 to about 0.10 wt. % of base catalyst is used, based on the total weight of all reaction medium components including the alkyl glucoside or alkyl polyglucoside, the glycerylation agent, and the lower esters of the fatty acid utilized for transesterification. The reaction is preferably conducted under vacuum to distill water vapor formed during the reaction. The vacuum can range from about 125 to about 1 mm Hg in one aspect, 50 to about 3 mm Hg in another aspect, and from 10 to about 3 mm Hg in a further aspect. An inert gas sparge using a gas such as argon, helium or nitrogen can be maintained in the reaction medium to facilitate the distillation and removal of water vapor.

The reaction and its completion can conveniently be monitored using standard IR spectroscopy, high pressure liquid chromatography (HPLC) or gas chromatography (GC) techniques. Reaction times typically run between about 24 to about 72 hours. In practice, additional time under reaction conditions may be used to ensure complete reaction. Following completion of the reaction, the product is cooled and isolated by conventional techniques known in the art.

Emulsifier Compositions

The compounds of the invention are used as an emulsifier in a wide variety of applications such as, for example, in food and/or personal care products. They can also be utilized as solubilizers, emollients, humectants, dispersants and spreading aids. The esterified glycerylated alkyl glucosides and polyglucosides are particularly suitable for preparing emulsions and dispersions in which the water phase is the external phase, e.g., O/W emulsions. By employing suitable hydrophobic co-emulsifiers, the esterified glycerylated alkyl glucosides and polyglucosides of the invention can also be used for producing emulsions and dispersions in which the aqueous phase forms the internal phase, e.g., W/O emulsions.

In one aspect of the invention, the compositions are employed as emulsifiers and dispersing agents for producing cosmetic or pharmaceutical preparations. These are cosmetic preparations which, through the use of O/W or W/O emulsifiers, are given a readily spreadable consistency because these emulsifier systems allow an oil or a fatty substance to be readily incorporated into an aqueous phase, or an aqueous phase to be readily incorporated into an oil or a fat, for example, creams, such as, skin and hair care creams, baby creams or sun protection creams, ointments, lotions or make-up. In health care preparations, such as, ointments or creams, O/W or W/O emulsifiers are required for the formulation of active ingredients. In home care formulations, such as, pastes waxes, polishes, and the like.

Non-limiting examples of personal care and cosmetic products in which the emulsifiers of the invention may be used are skin moisturizing creams, lotions, and sprays, anti-aging creams, lotions, and sprays, sunscreen creams, lotions, and sprays, skin lightening creams, lotions, and sprays self-tanning creams, lotions, and sprays, anti-acne creams, lotions, and sprays, skin exfoliating creams, lotions, and sprays, color cosmetic creams, lotions, and sprays, including liquid make-up and foundation, hair conditioning creams, lotions, and sprays, hair styling creams, lotions, and sprays, antiperspirant and deodorant gels, creams, lotions, and sprays, depilatory and shaving creams, lotions, and sprays, and hair coloring creams, lotions, and sprays.

A. Oil Phase

The oil phase includes all natural or synthetic oils and mixtures thereof. The oils may be volatile or non-volatile, or a mixture of both. An important feature of the invention is that the emulsifier described herein is capable of dispersing the oil phase in an O/W emulsion. The ability to disperse the oil phase is essentially independent of the type of oil phase. In addition, the amount of oil phase can be relatively high relative to the aqueous phase. The emulsifier of the invention can effectively emulsify any oil phase, even difficult to emulsify oil phases such as silicone oils and vegetable oils (e.g., sunflower oil). Accordingly, the O/W emulsion can be formulated to contain any type of oil phase, like silicones, esters, or hydrocarbons, in order to achieve a desired effect. Suitable oils include, but are not limited to vegetable oils, animal oils, hydrocarbon oils, fatty alcohols, fatty acid esters, silicone oils, oily UV absorbers and sunscreens, fragrance oils, and mixtures thereof.

Exemplary vegetable oils include, but are not limited to apricot stone, avocado oil, macadamia nut oil, olive oil, coconut oil, jojoba oil, corn oil, sunflower oil, palm oil, soybean oil, castor oil, peanut oil, walnut oil, rapeseed oil, almond oil, palm oil, coconut oil palm kernel oil, groundnut oil, wheat germ oil, cottonseed oil, lucerne oil, poppy oil, pumpkin oil, primrose oil, millet oil, barley oil, rye oil, wheat germ oil, safflower oil, candlenut oil, passiflora oil, hazelnut oil, shea butter, calophyllum oil, sysymbrium oil, and mixtures thereof.

Synthetically modified vegetable oils (mono-, di-, and triglycerides) derived through the esterification of glycerol, a monoglyceride, or a diglyceride with a fatty acid(s) also is suitable as the oil phase component. They are prepared by techniques well known in the art, or by glycerolysis of animal fats and vegetable oils in the presence of a base at elevated temperature and under an inert atmosphere (See RSC Green Chemistry Book Series, The Royal Society of Chemistry, *The Future of Glycerol: New Uses Of A Versatile Material*, Chapter 7, Mario Pagliaro and Michele Rossi, © 2008). Fatty acids suitable for use in the esterification reaction include saturated and unsaturated $C_8$-$C_{30}$ fatty acids.

Exemplary animal oils include, but are not limited to, neatsfoot oil, liquid fractions of beef tallow, lanolin, lanolin derivatives (e.g., isopropyl lanolate, isocetyl lanolate), tallow, mink oil, cholesterol, fish oil, sperm whale oil, and mixtures thereof.

Exemplary hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils typically contain about 12 to 19 carbon atoms. Branched chain hydrocarbon oils, including hydrocarbon polymers, typically will contain more than 19 carbon atoms. Specific non-limiting examples of these hydrocarbon oils include paraffin oil, mineral oil, petrolatum, liquid polyolefin oils, fluorinated and perfluorinated oils, saturated and unsaturated dodecane, isohexadecane, isododecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl substituted isomers, e.g., the permethyl-substituted isomers of hexadecane and eicosane, such as 2,2,4,4,6,6,8,8-octamethyl-10-methylundecane and 2,2,4,4,6,6-hexamethyl-8-methyl-nonane, available from Permethyl Corporation. Hydrocarbon polymers such as polybutene and polydecene are also useful. Mineral oils and petrolatums include cosmetic, USP and NF grades and are commercially available from Penreco under the Drakeol® and Penreco® trade names.

The liquid polyolefin oils are typically poly(α-olefins) that have been hydrogenated. Polyolefins for use herein can be prepared by the polymerization of $C_4$ to about $C_{14}$ olefinic monomers. Non-limiting examples of olefinic monomers for use in preparing the polyolefin liquids herein include ethylene, propylene, 1-butene, 1-pentene, 1-hexene, 1-octene, 1-decene, 1-dodecene, 1-tetradecene, and 1-hexadecene, branched isomers such as isobutylene, 4-methyl-1-pentene, and mixtures thereof. In one aspect, a suitable hydrogenated polyolefin is the copolymer of isobutylene and butene. A commercially available material of this type is Panalane® L-14E (INCI Name: Hydrogenated Polyisobutene) marketed by Lipo Chemicals Inc, Patterson, N.J.

Fluorinated oils include perfluoropolyethers described in European Patent No. EP 0 486 135 and the fluorohydrocarbon compounds described in International Patent Application Publication No. WO 93/11103. The fluoridated oils may also be fluorocarbons such as fluoramines, e.g., perfluorotributylamine, fluorinated hydrocarbons, such as perfluorodecahydronaphthalene, fluoroesters, and fluoroethers.

The fatty alcohols suitable for use in the compositions of the invention include, but are not limited to, the saturated and unsaturated $C_8$-$C_{30}$ fatty alcohols. Exemplary fatty alcohols include capryl alcohol, pelargonic alcohol, capric alcohol, decyl alcohol, undecyl alcohol, lauryl alcohol, myristyl alcohol, cetyl alcohol, isocetyl alcohol, stearyl alcohol, isostearyl alcohol, cetearyl alcohol, palmitoleyl alcohol, elaidyl alcohol, sterol, oleyl alcohol, linoleyl alcohol, elaidolinoleyl alcohol, linolenyl alcohol, ricinoleyl alcohol, arachidyl alcohol, icocenyl alcohol, behenyl alcohol, erucyl alcohol, lignoceryl alcohol, ceryl alcohol, montanyl alcohol, myricyl alcohol, and mixtures thereof. Fatty alcohols are widely available and can be obtained through the hydrogenation of esterified vegetable and animal oils and fats.

Suitable fatty acid esters are the mono-, di- or triesters of linear and/or branched mono-, di- or tricarboxylic acids having 2 to 44 carbon atoms with linear and/or branched saturated or unsaturated alcohols having 1 to 22 carbon atoms.

Monoesters suitable as oil components are, for example, the methyl esters and isopropyl esters of fatty acids having 12 to 22 carbon atoms, for example, methyl laurate, methyl stearate, methyl cocoate, methyl oleate, methyl erucate, isopropyl palmitate, isopropyl myristate, isopropyl stearate, isopropyl isostearate, or isopropyl oleate.

Other suitable monoesters are, for example, butyl stearate, hexyl laurate, isohexyl laurate, isodecyl neopentanoate, isooctyl stearate, lauryl lactate, isostearyl lactate, cetearyl octanoate isononyl palmitate, isononyl isononanoate, 2-ethylhexyl laurate, octyl stearate, decyl stearate, cetyl stearate, stearyl stearate, oleyl stearate, 2-hexyldecyl stearate, 2-ethylhexyl palmitate, cetyl palmitate, 2-octyldodecyl palmitate, myristyl myristate, oleyl myristate, decyl oleate, isodecyl oleate, oleyl oleate, oleyl erucate, or erucyl oleate, and esters which are obtainable from technical grade aliphatic alcohol cuts and technical grade, aliphatic carboxylic acid mixtures, e.g., esters of unsaturated fatty alcohols having 12 to 22 carbon atoms and saturated and unsaturated fatty acids having 12 to 22 carbon atoms, as are obtainable from animal and vegetable fats.

Diesters suitable as oil components are, for example, those prepared from dicarboxylic acids (e.g., oxalic, malonic, succinic, glutaric, adipic, pimelic, suberic, azelaic, sebacic, phthalic, isophthalic, terephthalic, maleic, glutaconic and traumatic acids) and linear and/or branched saturated or unsaturated alcohols having 1 to 22 carbon atoms. Examples of dicarboxylic acid esters include, but are not limited to, diisopropyl adipate, dibutyl adipate, dioctyl adipate, di(2-ethylhexyl) adipate, dibutyl sebacate or di(2-hexyldecyl) succinate, diisotridecyl acelate.

Diol esters prepared from a diol (e.g., glycols, polyglycols, and linear or branched diols) and a $C_6$ to $C_{22}$ linear or branched, saturated or unsaturated monocarboxylic acid can be employed as the oil component. Exemplary diol esters are, for example, ethylene glycol dioleate, ethylene glycol diisotridecanoate, propylene glycol di(2-ethylhexanoate), polypropylene glycol monooleate, polypropylene glycol monostearate, butanediol diisostearate and neopentyl glycol dicaprylate.

Triesters suitable as the oil component are, for example, those prepared from tricarboxylic acids (e.g., citric, isocitric, aconitic, carballylic, trimesic, trimellitic acid) and linear and/or branched saturated or unsaturated alcohols having 1 to 22 carbon atoms. Exemplary triesters include but are not limited to, trimethyl citrate, triethyl citrate, tristearyl citrate, triisopropyl citrate, triisostearyl citrate, trioctyldodecyl citrate, trioleyl citrate, triisodecyl citrate, triisopropyl citrate, tributyl citrate, tris(2-ethylhexyl)citrate, trioctyl trimellitate, and mixtures thereof.

Also suitable are the esterification products of aliphatic, difunctional alcohols having 2 to 36 carbon atoms with monofunctional saturated and unsaturated $C_8$ to $C_{30}$ fatty acids. Other polyhydric alcohol esters include the partial esters of polyglycerols. These esters contain 2 to 10 glycerol units and are esterified with 1 to 4 saturated or unsaturated, optionally hydroxylated $C_8$ to $C_{30}$ fatty acids. Representative partial esters of polyglycerols include, but are not limited to, diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, decaglycerol trihydroxystearate, and mixtures thereof.

Suitable silicone oils include, but are not limited to, polydimethylsiloxanes, methylphenylpolysiloxanes, silicones modified by amines, silicones modified by alcohols and fatty acids, cyclic polysiloxanes, and mixtures thereof. They can be volatile or non-volatile.

Silicone oils include polyalkyl, polyaryl siloxanes, or polyalkylaryl siloxanes which conform to the following formula:

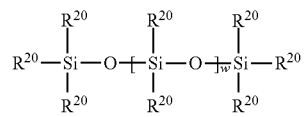

wherein $R^{20}$ is an aliphatic group, independently selected from alkyl, alkenyl, and aryl, $R^{20}$ can be substituted or unsubstituted, and w is an integer from 1 to about 8,000. Suitable unsubstituted $R^{20}$ groups for use in the present invention include, but are not limited to alkoxy, aryloxy, alkaryl, arylalkyl, arylalkenyl, alkamino, and ether-substituted, hydroxyl substituted, and halogen substituted aliphatic and aryl groups.

In one aspect of the invention, exemplary $R^{20}$ alkyl and alkenyl substituents include $C_1$-$C_5$ alkyl and $C_1$-$C_5$ alkenyl groups. In another aspect, $R^{20}$ is methyl. Exemplary aryl groups in the foregoing embodiments include phenyl and benzyl moieties.

Exemplary siloxanes are polydimethyl siloxane, polydiethylsiloxane, and polymethylphenylsiloxane. These siloxanes are available, for example, from Momentive Performance Materials in their Viscasil R and SF 96 series, and from Dow Corning marketed under the Dow Corning 200 series. Exemplary polyalkylaryl siloxane fluids that may be used include, for example, polymethylphenylsiloxanes. These siloxanes are available, for example, from Momentive Performance Materials as SF 1075 methyl phenyl fluid or from Dow Corning as 556 Cosmetic Grade Fluid, or from Wacker Chemical Corporation, Adrian, Mich., under the trade name Wacker-Belsil® PDM series of phenyl modified silicones (e.g., PDM 20, PDM 350 and PDM 1000).

Cyclic polysiloxanes (cyclomethicones) can be represented by the formula:

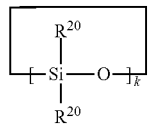

wherein the substituent $R^{20}$ is as defined above, and the number of repeat units, k, ranges from about 3 to about 7 in one aspect, and from 3 to 5 in another aspect. Additionally, $R^{20}$ and k can be selected so that the material is volitile or non-volatile. Aryl containing substituents include those which contain alicyclic and heterocyclic five and six member aryl rings and those which contain fused five or six member rings. The aryl rings can be substituted or unsubstituted. Substituents include aliphatic substituents, and can also include alkoxy substituents, acyl substituents, ketones, halogens (e.g., Cl and Br), amines, etc. Exemplary aryl containing groups include substituted and unsubstituted arenes, such as phenyl, and phenyl derivatives such as phenyls with $C_1$-$C_5$ alkyl or alkenyl substituents, e.g., allylphenyl, methyl phenyl and ethyl phenyl, vinyl phenyls such as styrenyl, and phenyl alkynes (e.g., phenyl $C_2$-$C_4$ alkynes). Heterocyclic aryl groups include substituents derived from furan, imidazole, pyrrole, pyridine, etc. Fused aryl ring substituents include, for example, naphthalene, coumarin, and purine.

Exemplary cyclomethicones are D4 cyclomethicone (octamethylcyclotetrasiloxane), D5 cyclomethicone (decamethylcyclopentasiloxane), D6 cyclomethicone (dodecamethylcyclohexasiloxane), and blends thereof (e.g., D4/D5 and D5/D6). Cyclomethicone and cyclomethicone blends are commercially available from Momentive Performance Materials Inc. as SF1202, SF 1214, SF1256, and SF1258, Dow Corning, Midland, Mich. under the Xiameter® cyclomethicone fluid product designations PMX-0244, PMX-245, PMX-246, PMX-345, and Dow Corning® 1401 fluid.

Suitable fragrance oils include extracts from natural raw materials, such as, essential oils, concretes, absolutes, resins, resinoids, balsams, and tinctures; hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane; aliphatic alcohols; cyclic alcohols; cycloaliphatic alcohols; aliphatic ketones; acyclic terpene alcohols; cyclic terpene alcohols; cyclic terpene aldehydes and ketones; and mixtures thereof. Additional fragrance oils are disclosed in U.S. Pat. No. 7,335,631, which is hereby incorporated by reference. Other suitable fragrance oils are disclosed below as fragrances and perfumes.

The emulsifying polymers of the present invention can stably emulsify oil(s) in water, even when the amount of an oil exceeds the solubility limit of the oil in a given aqueous solution of the polymer. Surprisingly, the present emulsifier polymer is further capable of stabilizing highly concentrated oil phase O/W emulsions, where the volume fraction of the oil phase in the emulsion can as high as 0.5 in one aspect, as high as 0.6 in another aspect, as high as 0.75 in still another aspect, as high as 0.85 in a further aspect, as high as 0.90 in a still further aspect, and as high as 0.95 in an additional aspect. By "volume fraction" is meant the ratio of the volume of the oil phase to the total volume of the emulsion (oil and water). In another exemplary embodiment, the volume fraction of the oil phase ranges from about 0.01 to about 0.95 in one aspect, from about 0.1 to about 0.85 in another aspect, from about 0.15 to about 0.75 in still another aspect, from about 0.25 to about 0.6 in a further aspect, and from about 0.35 to about 0.5 in an additional aspect based on the volume of the emulsion (oil and water).

In another embodiment, the emulsions of the present invention will comprise up to about 50 wt. % of the oily phase in one aspect, up to about 60 wt. % in another aspect and up to about 75 wt. % in still another aspect, up to about 85 wt. % in a further aspect, up to about 90 wt. % in a still further aspect, and up to about 95 wt. % in an additional aspect based on the total weight of the emulsion (oil and water). In another exemplary embodiment, the oil phase component ranges from about 1 to about 95 wt. % in one aspect, from about 5 to about 85 wt. % in another aspect, from about 10 to about 40 wt. % in still another aspect, and from about 15 to about 30 wt. % in a further aspect, based on the total weight of the oil, water and emulsifier components.

The emulsifier of the present invention is used in an amount suitable to stably disperse the oil phase in the continuous aqueous phase of an emulsified composition. In one aspect, the amount of emulsifier will range from about 1 to about 30 wt. %, from about 2 to 25 wt. %, from about 2.5 to about 15 wt. %, and from about 5 to about 10 wt. %, based on the total weight of the oil phase component.

The oil phase of the emulsions may further comprise an optional oil soluble or oil dispersible co-emulsifier having a hydrophilic-lipophilic balance (HLB) value of 6.5 or less in one aspect, 6 or less in another aspect, 5 or less in still another aspect, 4.5 or less in a further aspect, and 2 or less in an additional aspect. The addition of a co-emulsifier is particularly beneficial to stably emulsify triglyceride based oils (e.g., vegetable oils, and in particular sunflower oil) that often inherently contain fatty acids.

Non-limiting examples of the foregoing low HLB surfactants include, but are not limited to sorbitan esters (e.g., sorbitan laurate, sorbitan palmitate, sorbitan sesquiisostearate, sorbitan sesquioleate, sorbitan sesquistearate, sorbitan stearate, sorbitan oleate, sorbitan monoisostearate, sorbitan trisostearate, sorbitan trioleate, sorbitan tristearate, and mixtures thereof); glyceryl esters (e.g., glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, and mixtures thereof); polyglyceryl esters (e.g., polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof); glycol esters (e.g., glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, and mixtures thereof); sucrose esters (e.g., sucrose cocoate and sucrose laurate, and mixtures thereof); methyl glucose esters (e.g., Methyl Glucose Sesquistearate, Methyl Glucose Dioleate); ethoxylated methyl glucose esters (e.g, PEG-20 Methyl Glucose Sesquistearate); and mixtures thereof. The choice of co-emulsifier will be determined by formulator preference and the physical properties of a particular co-emulsifier. Additional emulsifiers are provided in the INCI Ingredient Dictionary and Handbook 11th Edition 2006, the disclosure of which is hereby incorporated by reference.

If a co-emulsifier is utilized in combination with the emulsifiers of the invention, the combined total amount of the invention emulsifiers and the co-emulsifiers will not exceed the weight percent ranges set forth above for the invention emulsifier when used alone. As is well-known in the art the ratio of emulsifier (invention emulsifier) to co-emulsifier (if optionally employed) will depend on the type of oil used, the amount, and its polarity (polar vs. non-polar). In one embodiment, the weight ratio of the invention emulsifier to optional co-emulsifier can range from about 100:1 to about 1:100 in one aspect, from about 10:1 to about 1:10 in another aspect, and from about 5:1 to about 1:5 in further aspect.

In another embodiment, the weight ratio of the invention emulsifier to the co-emulsifier, particularly when polar oils (e.g., fatty alcohols, esters and triglycerides) are utilized, ranges from about 50:1 to about 1:2 in one aspect, from about 15:1 to about 1:1 in another aspect, and from about 10:1 to about 2:1 in a further aspect.

B. Aqueous Phase

The carrier of the O/W emulsion (i.e., the continuous phase) comprises water. The water may be deionized, industrial soft water, or any suitable grade of water.

C. Optional Components

The O/W emulsions of the invention can be utilized in the formulation of optional components which include, but are not limited to, fragrances, perfumes, botanicals, particulate materials (e.g., exfoliants, and anti-dandruff agents), insoluble materials, opacifiers and pearlizing agents, humectants, emollients, antioxidants, deodorizing agents, pH adjusting agents, buffers, chelation agents, viscosity modifiers, structuring agents, deposition aids, and topically active compounds such as UV protection agents, sunscreens, insect repellents, antiperspirants, cosmeceuticals, pharmaceuticals, skin and hair conditioners, preservatives, and combinations thereof. The continuous phase and/or the dispersed oil phase (i.e., the discontinuous phase) can contain the optional components to improve the efficacy and aesthetics of the formulation, and to deliver benefits agents when topically applied to a surface, a substrate or to the hair and skin.

It is to be understood that the materials listed above and below can serve more than one function and that the listing of a material in any particular class is not intended as a limitation for that material, and that characterization of an additive or component as having a specific function does not exclude the additive or component from performing another function.

When utilized, each optional component(s) typically is included in an amount of from about 0.0001 to about 25 wt. % in one aspect, from about 0.01 to 20 wt. % in another aspect, from about 0.1 to about 15 wt. % in a still another aspect, from about 0.5 to about 10 wt. % in a further aspect, and from about 1 to about 5 wt. % in a still further aspect, based on the total weight of the O/W emulsion. The amounts employed will vary with the purpose and character of the product and can be readily determined by one skilled in the formulation arts and from the literature.

Fragrances and Perfumes

The fragrance and perfume components that may be used in the context of the invention include natural and synthetic fragrances, perfumes, scents, and essences and any other substances which emit a fragrance. As the natural fragrances, there are those of vegetable origin, such as oil extracts from flowers (e.g., lily, lavender, rose, jasmine, neroli, ylang-ylang), stems and leaves (geranium, patchouli, petitgrain, peppermint), fruits (aniseed, coriander, fennel, needle juniper), fruit skin (bergamot, lemon, orange), roots (mace, angelica, celery, cardamom, costus, iris, sweet flag), woods (pine tree, sandalwood, guaiacum wood, cedar, rosewood, cinnamon), herbs and grasses (tarragon, lemongrass, sage, thyme), needles and twigs (spruce, pine, European red pine, stone pine), and resins and balsam (galbanum, elemi, benzoin, myrrh, frankincense, opopanax), and those of animal origin, such as musk, civet, castoreum, ambergris, or the like, and mixtures thereof.

Examples of synthetic fragrances and perfumes are the aromatic esters, ethers, aldehydes, ketones, alcohols, and hydrocarbons including, but are not limited to, benzyl acetate, phenoxyethyl isobutylate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styralyl propionate, and benzyl salicylate; benzylethyl ether; straight chain alkanals having 8 to 18 carbon atoms, citral, citronellal, citronellyloxyaldehyde, cyclamen aldehyde, hydroxycitronellal, lilial, and bougeonal; ionone compounds, α-isomethyl ionone, and methyl cedryl ketone; anethole, citronellol, eugenol, isoeugenol, geraniol, lavandulol, nerolidol, linalool, phenylethyl alcohol, and terpineol, alpha-pinene, terpenes (e.g., limonene), and balsams, and mixtures thereof.

Botanicals

Suitable botanical agents may include, for example, extracts from Echinacea (e.g., sp. angustifolia, purpurea, pallida), yucca glauca, willow herb, basil leaves, Turkish oregano, carrot root, grapefruit, fennel seed, rosemary, tumeric, thyme, blueberry, bell pepper, blackberry, spirulina, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, and witch hazel. Botanical extracts may also include, for example, chlorogenic acid, glutathione, glycrrhizin, neohesperidin, quercetin, rutin, morin, myricetin, absinthe, and chamomile.

Particulates

Suitable particulate materials include pigments, exfoliants, and anti-dandruff agents. Exemplary pigments are metal compounds or semi metallic compounds and may be used in ionic, nonionic or oxidized form. The pigments can be in this form either individually or in admixture or as individual mixed oxides or mixtures thereof, including mixtures of mixed oxides and pure oxides. Examples are the titanium oxides (e.g., $TiO_2$), zinc oxides (e.g., ZnO), aluminum oxides (for example, $Al_2O_3$), iron oxides (for example, $Fe_2O_3$), manganese oxides (e.g., MnO), silicon oxides (e.g., $SiO_2$), silicates, cerium oxides, zirconium oxides (e.g., $ZrO_2$), barium sulfate ($BaSO_4$), nylon-12, and mixtures thereof.

Other examples of pigments include thermochromic dyes that change color with temperature, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide nanoparticles, barium oxide, ultramarine blue, bismuth citrate, hydroxyapatite, zirconium silicate, carbon black particles, and the like.

Numerous cosmetically useful particulate exfoliating agents are known in the art, and the selection and amount is determined by the exfoliating effect desired from the use of the composition, as recognized by those skilled in the cosmetic arts. Useful exfoliating agents include, but are not limited to, natural abrasives, inorganic abrasives, synthetic polymers, and the like, and mixtures thereof. Representative exfoliants include, but are not limited to, ground or powdered pumice, stone, zeolites, nut shells (e.g., almond, pecan, walnut, coconut, and the like), nut meals (e.g., almond, and the like), fruit pits (e.g., apricot, avocado, olive, peach, and the like), hulls, seed and kernel (e.g., oat bran, corn meal, rice bran, grape seed, kiwi seed, wheat, jojoba seed, loofah seed, rose hip seed, and the like), plant matter (e.g., tea tree leaves, corn cob, fruit fibers, seaweed, loofah sponge, microcrystalline cellulose, and the like), bivalve shells (oyster shell, and the like), calcium carbonate, dicalcium pyrophosphate, chalk, silica, kaolin clay, silicic acid, aluminum oxide, stannic oxide, sea salt (e.g., Dead Sea salt), talc, sugars (e.g., table, brown, and the like), polyethylene, polystyrene, microcrystalline polyamides (nylons), microcrystalline polyesters, polycarbonates, and stainless steel fibers. The foregoing exfoliants can be used in the form of granules, powders, flours, and fibers.

Suitable anti-dandruff agents that can be employed in the compositions of the present invention include, but are not limited to, sulfur, zinc pyrithione, zinc omadine, miconazole nitrate, selenium sulfide, piroctone olamine, N,N-bis(2-hydroxyethyl)undecanamide, cade oil, pine tar, coal tar, *Allium cepa* extract *Picea abies* extract, and Undecyleneth-6, and the like, and mixtures thereof.

Insoluble Materials

Insoluble materials suitable for use in the present compositions include, but are not limited to, clay, swellable clay, laponite, gas bubbles, liposomes, microsponges, cosmetic beads and flakes. Cosmetic beads, flakes and capsules can be included in a composition for aesthetic appearance or can function as microencapsulants for the delivery of benefit agents to the skin and/or the hair. Exemplary bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.).

Opacifiers and Pearlizing Agents

Some formulations are often opacified by deliberately incorporating pearlescent materials therein to achieve a cosmetically attractive pearl like appearance, known as pearlescence. An opacifier often is included in a composition to mask an undesirable aesthetic property, such as to improve the color of a composition that is darkened due to the presence of a particular ingredient, or to mask the presence of particulate matter in the composition. Opacifiers also are included in compositions to improve the aesthetics and consumer acceptance of an otherwise esthetically unpleasing composition. For example, an opacifier can impart a pearlescent appearance to a clear composition, thereby communicating an appearance of creaminess, mildness and body to the consumer. Persons skilled in the art are aware of problems faced by formulators in consistently preparing a stable pearlescent formulation. A detailed discussion is found in the article "Opacifiers and Pearling Agents in Shampoos" by Hunting, *Cosmetic and Toiletries*, Vol. 96, pages 65-78 (July 1981), incorporated herein by reference.

The opacifying or pearlescent material can be selected from a number of different chemical classes including inorganic compounds, e.g., various aluminum and magnesium salts, and organic compounds, like fatty alcohols, fatty esters and various polymers and copolymers including, but is not limited to, ethylene glycol mono-stearate, ethylene glycol distearate, polyethylene glycol distearate, stearic alcohol, bismuth oxychloride coated mica, mica coated metal oxides (e.g., titanium dioxide, chromium oxide, iron oxides), myristyl myristate, guanine, glitter (polyester or metallic), and mixtures thereof. Other pearlescent materials can be found in U.S. Pat. Nos. 4,654,207, 5,019,376, and 5,384,114, which are herein incorporated by reference. A representative listing of opacifiers/pearlescent materials is found in the CTFA Cosmetic Ingredient Handbook, J. Nikitakis, ed., The Cosmetic, Toiletry and Fragrance Association, Inc., Washington, D.C., 1988, at page 75.

Humectants

Humectants suitable for use in the composition of the invention include, but are not limited to, glycerol, polyglycerols, sorbitol, propane-1,2-diol, butane-1,2,3-triol, polyethylene glycols, glucose, mannitol, xyliyol, and mixtures thereof.

Emollients

Emollients may include silicone oils, functionalized silicone oils, hydrocarbon oils, fatty alcohols, fatty alcohol ethers, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The emollients may be either saturated or unsaturated, have an aliphatic character and be straight or branched chained or contain alicyclic or aromatic rings.

Antioxidants

An antioxidant functions, among other things, to scavenge free radicals from skin to protect the skin from environmental aggressors. Examples of antioxidants that may be used in the present compositions include, but are not limited to, compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; and mixtures thereof. Other suitable antioxidants are those that have one or more thiol functions (—SH), in both reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur.

Deodorizing Agents

Deodorizing agents counteract, mask or eliminate body odors that are formed through the action of skin bacteria on apocrine perspiration which results in the formation of unpleasant smelling degradation products. Accordingly, suitable deodorizing agents include, inter alia, microbial inhibitors, enzyme inhibitors, odor absorbers and odor maskers. Undecylenic acid and ester derivatives of undecylenic acid have been found to possess significant deodorizing activity. Polyoxyalkylene and simple alkyl esters of undecylenic acid (e.g., methyl undecylenate and ethyl undecylenate) are well-known deodorizers. Esterase inhibitors such as the trialkyl citrates (e.g., trimethyl citrates, triethyl citrates, tripropyl citrates, triisopropyl citrates, tributyl citrates) are useful deodorizers. Additional examples of useful esterase inhibitors are sterol sulfates and phosphates, such as, for example, lanosterine-, cholesterine-, campesterine-, stigmasterine- and sitosterine sulfates and phosphates, respectively; dicarbonic acids and their esters, such as, for example, glutaric acid, glutaric acid monoethylester, glutaric acid diethylester, adipinic acid, adipinic acid monoethylester, adipinic acid diethylester, malonic acid and malonic acid diethylester, hydroxycarbonic acids and their esters such as, for example, citric acid, malonic acid, tartaric acid or tartaric acid diethylester. Other deodorizing agents include deodorant compounds (e.g., 2-amino-2-methyl-1-propanol (AMP), ammonium phenolsulfonate; benzalkonium chloride; benzethonium chloride, bromochlorophene, cetyltrimethylammonium bromide, cetyl pyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarban, triclosan, zinc phenolsulfonate, zinc ricinoleate, and mixtures thereof); and suitable mixtures of any of the above.

pH Adjusting Agents

The pH of the compositions of the present invention can be adjusted with any combination of acidic and/or basic pH adjusting agents known to the art. Acidic materials include organic acids and inorganic acids, for example, acetic acid, citric acid, tartaric acid, alpha-hydroxy acids, beta-hydroxy acids, salicylic acid, lactic acid, glycolic acid, and natural fruit acids, or inorganic acids, for example, hydrochloric acid, nitric acid, sulfuric acid, sulfamic acid, phosphoric acid, and combinations thereof.

Basic materials include inorganic and organic bases, and combinations thereof. Examples of inorganic bases include but are not limited to the alkali metal hydroxides (especially sodium, potassium, and ammonium), and alkali metal salts such as sodium borate (borax), sodium phosphate, sodium pyrophosphate, and the like; and mixtures thereof. Examples of organic bases include but are not limited to triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, tromethamine (2-amino 2-hydroxymethyl-1,3-propanediol), and PEG-15 cocamine.

Buffer Agents

Buffering agents can be used in the compositions of the invention. Suitable buffering agents include, but are not limited to, alkali or alkali earth metal carbonates, phosphates, bicarbonates, citrates, borates, acetates, acid anhydrides, succinates, and the like, such as sodium phosphate, sodium citrate, sodium acetate, sodium bicarbonate, and sodium carbonate.

The pH adjusting agent(s) and/or buffering agent is utilized in any amount necessary to obtain and/or maintain a desired pH value in the composition. The pH of the emulsions of the invention range from about 2 to about 10 in one aspect, from about 3 to about 9 in another aspect, and from about 3.5 to about 8 in a further aspect.

Chelation Agents

Chelating agents can be employed to stabilize the personal care, home care, health care, and institutional care compositions of the invention against the deleterious effects of metal ions. When utilized, suitable chelating agents include EDTA (ethylene diamine tetraacetic acid) and salts thereof such as disodium EDTA, citric acid and salts thereof, cyclodextrins, and the like, and mixtures thereof.

Viscosity Modifiers

The emulsion can be thickened by using a thickener in the external aqueous phase. The oil phase of the emulsion may be thickened with waxes, hydrophobically modified metal oxides, and layered silicates and aluminates such as fumed silica, fumed alumina, and smectite clays. The compositions of the present invention may further comprise a suspending agent at concentrations effective for suspending water insoluble material in dispersed form in the compositions or for modifying the viscosity of the composition. Thickeners and suspending agents useful herein for the external phase include anionic polymers and nonionic polymers. Useful herein are vinyl polymers such as cross linked acrylic acid polymers with the INCI name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, cassia gum, xanthan gum, gum arabic, tragacanth, galactan, carob gum, guar gum, karaya gum, carrageenan, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers available under the trade names Carbopol® 934, Carbopol® 940, Carbopol® 950, Carbopol® 980, and Carbopol® 981 polymers, all available from Lubrizol Advanced Materials, Inc., acrylates/steareth-20 methacrylate copolymer having the trade name Acrysol™ 22 available from Rohm and Haas (Dow Chemical Company), nonoxynyl hydroxyethylcellulose available under the trade name Amercell™ Polymer HM-1500 available from Amerchol (Dow Chemical Company); methylcellulose available under the trade name Benecel®, hydroxyethyl cellulose available under the trade name Natrosol®, hydroxypropyl cellulose available under the trade name Klucel®, cetyl hydroxyethyl cellulose available under the trade name Polysurf® 67, all supplied by Hercules (Ashland Inc.), ethylene oxide and/or propylene oxide based polymers available under the trade names Carbowax® PEGs, Polyox™ resins, and Ucon® Fluids, all supplied by Amerchol (Dow Chemical Company).

Structuring Agents

The compositions of the present invention may contain a structuring agent. Structuring agents are especially suitable in the emulsions of the present invention, for example, in the oil-in-water emulsions of the present invention. Without being limited by theory, it is believed that the structuring agent assists in providing rheological characteristics (for example yield and structural characteristics) to the composition which contribute to the stability of the composition.

The structuring agents of the present invention may be selected from stearic acid, palmitic acid, stearyl alcohol, cetyl alcohol, behenyl alcohol, palmitic acid, the polyethylene glycol ether of stearyl alcohol having an average of from about 1 to about 5 ethylene oxide units, the polyethylene glycol ether of cetyl alcohol having an average of from about 1 to about 5 ethylene oxide units, and mixtures thereof. In one aspect, structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. In another aspect, structuring agents are selected from the group consisting of stearic acid, palmitic acid, stearyl alcohol, cetyl alcohol, behenyl alcohol, steareth-2, and mixtures thereof.

Deposition Aids

The deposition aids of the compositions of the present invention can be selected from polymers which carry a cationic charge. The polymers are cationic derivatives of natural and synthetic polymers. In one aspect the naturally derived cationic polymers are derivatives of polygalactomannans such as guar and cassia gum. Suitable cationic guar gum derivatives are those having the INCI designation Guar Hydroxypropyltrimonium Chloride, available commercially from Rhodia Novecare under the trade names Jaguar® C13S, Jaguar® C15, Jaguar® C16 and Jaguar® C17 guar derivatives. Suitable cationic cassia derivatives having the INCI Name Cassia Hydroxypropyltrimonium Chloride are available from Lubrizol Advanced Materials, Inc. under the trade names Sensomer™ CT-250 and Sensomer™ CT-400 polymers. Other suitable deposition aids include quaternary nitrogen substituted cellulose ether derivatives INC designation Polyquaternium-10 such as those commercially available under the Ucare™ JR-400, JR-125, JR-30M, LR-400, LR-30M and LK polymer series trade names from Dow Chemical Company.

Suitable cationic synthetically derived polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the desired pH of the composition. Any anionic counterions can be used in association with the cationic polymers so long as the polymers remain soluble in the water phase of the composition and so long as the counterions are physically and chemically compatible with the essential components of the emulsified composition or do not otherwise unduly impair product performance, stability or aesthetics. Non-limiting examples of such counterions include halides (e.g., chlorine, fluorine, bromine, and iodine), sulfate and methylsulfate.

The cationic nitrogen containing moiety of the synthetic cationic polymer is generally present as a substituent on all, or more typically on some, of the monomer units thereof. Thus, the cationic polymer for use in the shampoo composition includes homopolymers, copolymers, terpolymers, and so forth, of quaternary ammonium or cationic amine substituted monomer units, optionally in combination with non-cationic monomers. Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers have from $C_1$ to $C_7$ alkyl groups in one aspect and from $C_1$ to $C_3$ alkyl groups in another aspect. Other suitable monomers include vinyl esters, vinyl alcohol (made by hydrolysis of polyvinyl acetate), maleic anhydride, propylene glycol, and ethylene glycol.

Suitable cationic protonated amino and quaternary ammonium monomers, for inclusion in the cationic polymers of the shampoo composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are $C_1$-$C_7$ hydrocarbyls in one aspect and $C_1$-$C_3$, alkyls in another aspect.

Other suitable cationic polymers for use in the emulsified compositions include copolymers of 1-vinyl-2-pyrrolidone and 1-vinyl-3-methylimidazolium salt (e.g., chloride salt) (INCI name: Polyquaternium-16) such as those commercially available from BASF Corporation under the LUVIQUAT™ trade name (e.g., product designations FC 370 and FC 905); copolymers of 1-vinyl-2-pyrrolidone and dimethylaminoethyl methacrylate (INCI name: Polyquaternium-11) such as those commercially available from Ashland Inc. under the GAFQUAT trade name (e.g., product designation 755N); cationic diallyl quaternary ammonium containing polymers, including, for example, dimethyldiallylammonium chloride homopolymer, copolymers of acrylamide and dimethyldiallylammonium chloride (INCI name: Polyquaternium 6 and Polyquaternium 7), such as those available under the MERQUAT™ trade name (e.g., product designations 100 and 550) from Lubrizol Advanced Materials, Inc.; amphoteric copolymers of acrylic acid including copolymers of acrylic acid and dimethyldiallylammonium chloride (INCI name: Polyquaternium-22) such as available from Lubrizol Advanced Materials, Inc. under the Merquat trade name (e.g., product designations 280 and 295), terpolymers of acrylic acid with dimethyldiallylammonium chloride and acrylamide (INCI name: Polyquaternium-39) such as those available from Lubrizol Advanced Materials, Inc. under the Merquat™ trade name (e.g., product designations 3300 and 3331), and terpolymers of acrylic acid with methacrylamidopropyl trimethylammonium chloride and methylacrylate (INCI name: Polyquaternium-47) available from Lubrizol Advanced Materials, Inc. under the Merquat™ trade name (e.g., product designation 2001).

The forgoing deposition aids serve a dual function in that they provide conditioning and sensory aesthetics to the hair and/or skin.

UV Protection Agents

UV protective agents (UV-B and UV-A) are organic compounds which are able to absorb ultraviolet rays and release the absorbed energy in the form of longer wave radiation such as heat. The UV protective agents suitable for use herein may be classified into groups based upon their chemical structure: organic camphor derivatives, para-amino benzoates; salicylates; cinnamates; benzophenones; benzalmalonates, triazine derivatives, and miscellaneous compounds. The UV protective agents may be oil-soluble or water-soluble. Examples of oil soluble UV-B protective agents include, but are not limited to, 3-benzylidenecamphor and derivatives thereof, e.g., 3-(4-methylbenzylidene)camphor, 4-aminobenzoic acid derivatives, such as 2-ethylhexyl 4-(dimethylamino)benzoate, 2-ethylhexyl 4-(dimethylamino)benzoate and amyl 4-(dimethylamino)benzoate; esters of cinnamic acid, such as 2-ethylhexyl 4-methoxycinnamate, isopentyl 4-methoxycinnamate, 2-ethylhexyl 2-cyano-3-phenylcinnamate (octocrylene); esters of salicylic acid, such as 2-ethylhexyl salicylate, 4-isopropylbenzyl salicylate, homomenthyl salicylate; derivatives of benzophenone, such as 2-hydroxy-4-methoxybenzophenone, 2-hydroxy-4-methoxy-4'-methylbenzophenone, 2,2'-dihydroxy-4-methoxybenzophenone; esters of benzalmalonic acid, such as di-2-ethylhexyl 4-methoxybenzalmalonate; triazine derivatives, such as, for example, 2,4,6-trianilino(p-carbo-2'-ethyl-1'-hexyloxy)-1,3,5-triazine and octyltriazone; and propane-1,3-diones, such as 1-(4-tert-butylphenyl)-3-(4'-methoxyphenyl)propane-1,3-dione, and menthyl anthralinate and digalloyl trioleate.

Suitable water soluble UV-B protective agents include, but are not limited to, 2-phenylbenzimidazole-5-sulfonic acid and the alkali metal, alkaline earth metal, ammonium, alkylammonium, alkanolammonium and glucammonium salts thereof; sulfonic acid derivatives of benzophenone, such as 2-hydroxy-4-methoxybenzophenone-5-sulfonic acid and its salts; sulfonic acid derivatives of 3-benzylidenecamphor, such as 4-(2-oxo-3-bornylidenemethyl)benzenesulfonic acid, and 2-methyl-5-(2-oxo-3-bornylidene)sulfonic acid and salts thereof. Mixtures of the oil soluble and water soluble UV protective agents can be used in the emulsions of the invention.

Suitable typical UV-A protective agents include, but are not limited to, derivatives of benzoylmethane, such as 1-(4'-tert-butylphenyl)-3-(4'-methoxyphenyl)propane-1,3-dione and 1-phenyl-3-(4'-isopropylphenyl)propane-1,3-dione. The UV-A and UV-B filters can of course also be used in mixtures. Additional UV protective agents are disclosed in U.S. Pat. Nos. 5,169,624; 5,543,136; 5,849,273; 5,904,917; 6,224,852; 6,217,852; and Segarin et al., chapter VII, pages 189 of Cosmetics Science and Technology, and Final Over-the-Counter Drug Products Monograph on Sunscreens (Federal Register, 1999: 64:27666-27963), all of which are incorporated herein by reference.

Sunscreens

The sunscreens are insoluble or particulate substances that provide a physical barrier against UV radiation on the skin. Insoluble pigments are suitable for this purpose, namely finely disperse metal oxides or salts, such as, for example, titanium dioxide, zinc oxide, iron oxide, aluminum oxide, cerium oxide, zirconium oxide, silicates (talc), barium sulfate and zinc stearate. In one aspect, the particles have an average diameter of less than 100 nm, between 5 and 50 nm in another aspect, and between 15 and 30 nm in still another aspect. Typically, they have a spherical shape, although it is also possible to use particles which have an ellipsoidal or plate-like shape or a shape which deviates in some other way from the spherical configuration. A relatively new class of photoprotective filters are micronized organic pigments, such as, for example, 2,2'-methylenebis{6-(2H-benzotriazol-2-yl)-4-(1,1,3,3-tetramethylbutyl)phenol} with a particle size of less than 200 nm.

Insect Repellents

An insect repellent is any compound or composition which deters insects from a host. Suitable insect repellents useful in the compositions of the invention include, but are not limited to, N,N-diethyl-m-toluamide (DEET), pentane-1,2-diol or 3-(N-n-butyl-N-acetylamino)-propionic acid ethyl ester), dihydronepetalactone (DHN), butylacetylaminopropionate, natural pyrethroids such as the extract of the ground flowers of Chrysanthemum cinerariaefolium or C coccineum, and citronella oil.

Antiperspirants

Various antiperspirant agents that can be utilized according to the present invention include conventional antiperspirant metal salts and complexes of metal salts. In one aspect of the invention the metal salts and metal salt complexes utilized as the antiperspirant agents are acidic and are based on aluminum and zirconium and combinations thereof. These salts include but are not limited to aluminum halides, aluminum hydroxyhalides, aluminum sulfate, zirconium (zirconyl) oxyhalides, zirconium (zirconyl) hydroxyhalides, and mixtures or complexes thereof. Complexes of aluminum and zirconium salts include aluminum and zirconium salt complexes with amino acids, such as, for example, glycine or complexes with a glycol, such as, for example, propylene glycol (PG) or polyethylene glycol (PEG). Exemplary antiperspirant agents include but are not limited to aluminum chloride, aluminum chlorohydrate, aluminum dichlorohydrate, aluminum sesquichlorohydrate, zirconyl hydroxychloride, aluminum chlorohydrex PEG (aluminum chlorohydrex polyethylene glycol), aluminum chlorohydrex PG (aluminum chlorohydrex propylene glycol), aluminum dichlorohydrex PEG (aluminum dichlorohydrex polyethylene glycol), aluminum dichlorohydrex PG (aluminum dichlorohydrex propylene glycol), aluminum sesquichlorohydrex PEG (aluminum sesquichlorohydrex polyethylene glycol), aluminum sesquichlorohydrex PG (aluminum sesquichlorohydrex propylene glycol), aluminum zirconium trichlorohyrate, aluminum zirconium tetrachlorohyrate, aluminum zirconium pentachlorohyrate, aluminum zirconium octachlorohyrate, aluminum zirconium chlorohydrex GLY (aluminum zirconium chlorohydrex glycine), aluminum zirconium trichlorohydrex GLY (aluminum zirconium trichlorohydrex glycine), aluminum zirconium tetrachlorohyrex GLY (aluminum zirconium tetrachlorohyrex glycine), aluminum zirconium pentachlorohyrex GLY (aluminum zirconium pentachlorohyrex glycine), and aluminum zirconium octachlorohyrex GLY (aluminum zirconium octachlorohyrex glycine). Other antiperspirant agents include ferric chloride and zirconium powder. Mixtures of any of the foregoing antiperspirant agents are also suitable for use in the present invention.

Pharmaceutical and Cosmeceutical Actives

The compositions of the present invention can be formulated with at least one skin and/or hair care active (e.g., pharmaceutical and/or a cosmeceutical active compound to deliver a desired benefit effect when topically applied to the skin, hair and nails). These compounds may be soluble in oil or water, and may be present primarily in the oil phase or the water phase of the present compositions. Suitable benefit agents include, but are not limited to, vitamins, peptides, sugar amines, oil control agents, self-tanning actives, anti-acne actives, desquamation actives, skin lightening agents, depilatories, astringents, flavonoids, protease inhibitors, hair growth stimulating agents, anti-cellulite agents, anti-stretch mark actives, anti-wrinkle actives, lip plumping agents, anti-inflammatory and analgesic agents, anti-microbial and anti-fungal actives, and combinations thereof.

As used herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, $C_1$-$C_{18}$ nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition may comprise a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

The composition may comprise one or more peptides. As used herein, "peptide" refers to peptides containing ten or fewer amino acids, their derivatives, isomers, and complexes with other species such as metal ions (for example, copper, zinc, manganese, and magnesium). Peptide refers to both naturally occurring and synthesized peptides. In one aspect, the peptides are di-, tri-, tetra-, penta-, and hexa-peptides, their salts, isomers, derivatives, and mixtures thereof. Peptide derivatives also useful herein include lipophilic derivatives, e.g., palmitoyl derivatives, such as, for example, palmitoyl-lys-thr-thr-lys-ser, palmitoyl-gly-his-lys, their derivatives, and combinations thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EE-MQRR; Argireline), and Cu-histidine-glycine-glycine (Cu-HGG, also known as IAMIN®). The compositions may comprise from about $1\times10^{-7}\%$ to about 20%, alternatively from about $1\times10^{-6}\%$ to about 10%, and alternatively from about $1\times10^{-5}\%$ to about 5% of the peptide.

The composition may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt).

The composition may comprise one or more compounds for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof.

The composition may comprise one or self-tanning actives for giving the skin an artificial suntanned appearance. Examples of self-tanning compounds are mono- or polycarbonyl compounds such asisatin, alloxan, ninhydrin, glyceraldehyde, mesotartaric aldehyde, glutaraldehyde, erythrulose, tyrosine, tyrosine esters, and dihydroxyacetone (DHA), 1,3,-dihydroxy-2-propanone).

Exemplary anti-acne compounds include acidic agents such as alpha-hydroxy acids (ANAs), beta-hydroxy acids (BHAs), alpha amino acids, alpha-keto acids (AKAs), acetic acid, azelaic acid, and mixtures thereof. Other anti-acne compounds include resorcinol, sulfur, salicylic acid, erythromycin, zinc, and benzoyl peroxide. Suitable anti-acne actives are described in further detail in U.S. Pat. No. 5,607,980.

The composition may comprise a safe and effective amount of a desquamation active for improving the texture and smoothness of the skin. Suitable examples comprise sulfhydryl compounds and zwitterionic surfactants which are described in U.S. Pat. No. 5,681,852.

The composition may comprise a skin-lightening agent. Suitable skin-lightening agents include kojic acid, arbutin, tranexamic acid, ascorbic acid and derivatives (e.g., magnesium ascorbyl phosphate or sodium ascorbyl phosphate or other salts of ascorbyl phosphate), ascorbyl glucoside, fatty esters of ascorbyl acid, such as ascorbyl palmitate, ascorbyl stearate, and the like Other suitable skin lightening materials include undecylenoyl phenylalanine aloesin, kojic acid, hydroquinone, arbutin, fruital, vegetal or plant extracts, such as lemon peel extract, chamomile, green tea, paper mulberry extract, and the like.

The composition may comprise a depilatory such as calcium and sodium hydroxide, calcium or sodium thioglycolate, and mixtures thereof.

The composition may comprise an astringent such as alum, oatmeal, yarrow, witch hazel, bayberry, and isopropyl alcohol.

The composition compositions may comprise a flavonoid. The flavonoid can be a synthetic material or obtained as extracts from natural sources, which also further may be derivatized. Examples of flavonoids suitable for use in the present invention are flavanones selected from unsubstituted flavanones, monosubstituted flavanones, and mixtures thereof; chalcones selected from unsubstituted chalcones, monosubstituted chalcones, disubstituted chalcones, trisubstituted chalcones, and mixtures thereof; flavones selected from unsubstituted flavones, monosubstituted flavones, disubstituted flavones, and mixtures thereof; one or more isoflavones; coumarins selected from unsubstituted coumarins, monosubstituted coumarins, disubstituted coumarins, and mixtures thereof; chromones selected from unsubstituted chromones, monosubstituted chromones, disubstituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, $C_1$-$C_8$ alkyl, $C_1$-$C_4$ alkoxyl, O-glycoside, and the like or a mixture of these substituents.

Specific examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2', 4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof. Additional examples of suitable flavonoids are also disclosed in U.S. Pat. No. 6,235,773.

The composition may comprise protease inhibitors including, but are not limited to, hexamidine compounds (e.g., hexamidine diisethionate), vanillin acetate, menthyl anthranilate, soybean trypsin inhibitor, Bowman-Birk inhibitor, and mixtures thereof.

Hair growth stimulating agents may comprise any agent which stimulates hair growth and/or prevents hair loss, or thinning, including but are not limited to polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, siNA, siRNA, dsRNA, dsDNA, anti-senseDNA, nucleic acids, synthetic molecules, and combinations thereof, which may be employed to achieve the therapeutic effect on stimulation of hair growth and/or prevention of loss of hair e.g., the eyelid, eyebrow, scalp, and skin.

Non-limiting examples of prostaglandins are those of the A, F and E types. Prostaglandin derivatives that exhibit high pharmacological activity and no or only very small side effects, such as 13,14-dihydro-15-dehydro-17-phenyl-18,19, 20-trinor-PGF2α and its carboxylic acid esters.

Examples of pharmaceutical hair growth stimulating agent and/or hair growth stimulating agent and/or hair density increasing agent and/or hair loss prevention agents include, but are not limited to prostaglandin A2, prostaglandin F2α, prostacyclin, prostaglandin EI, prostaglandin E2, 7-thiaprostaglandin EI, 16,17,18,19,20-pentanol-15-cyclohexyl-7-thiaprostaglandin EI, 16,17,18, 19,20-pentanol-15-cyclopentyl-7-thiaprostaglandin EI, 16,16-dimethyl-7-thiaprostaglandin EI, 17,20-dimethyl-7-thiaprostaglandin EI, 16,17,18,19,20-pentanol-15-cyclohexyl-δ2-7-thiaprostaglandin EI, 16,16-dimethyl-52-prostaglandin EI, 7-fluoroprostacyclin, 5-fluoroprostacyclin, 16,17,18,19,20-pentanol-15-cycrohexylprostacyclinor 16,17,18,19,20-pentanol-15-cycropentylprostacyclin. Other examples of prostaglandins and prostaglandin analogues which may be used in the instant invention include, but are not limited to, Arbaprostil, Carboprost, Enprostil, Bimatoprost, Bemeprost, Latanaoprost, Limaprost, Misoprostol, Minoxidil, Ornoprostil, Prostacyclin, Prostaglandin EI, Prostaglandin E2, Prostaglandin F2a, Rioprostil, Rosaprostol, Sulprostone, Travaprost, Trimoprostil, and Viprostol. Other examples of hair growth stimulating and/or hair loss prevention agents include, but are not limited to 15-hydroxyprostaglandin dehydrogenase (15-PGDH) inhibitors, including but not limited to pyrazolecarboxamide compounds, tetrazole compounds, and 2-alkylideneaminooxyacetamide compounds (see U.S. Patent Application Publication Numbers 2006/0026775, 2004/0052760, and 2004/0235831).

Other non-limiting examples of hair growth stimulating agents are hexamidine, butylated hydroxytoluene (BHT), hexanediol, panthenol and pantothenic acid derivatives, their isomers, salts and derivatives, and mixtures thereof.

The composition may comprise anti-stretch mark actives including arabignogalactan, lupeol, soya peptides, tripeptides composed of the amino acids glycine, histidine and lysine, *sophora* (*Sophora japonica*) flower extract, chlorophyceae (*Enteromorpha compressa*) extract, peptide extract of avocado, panthenol, and mixtures thereof.

The composition may comprise an effective amount of an anti-cellulite agent. Suitable agents may include, but are not limited to, xanthine compounds caffeine, theophylline, theobromine, and aminophylline.

The compositions of the present invention may further contain one or more anti-wrinkle actives. Exemplary anti-wrinkle actives suitable for use include retinol and retinol derivatives, sulfur-containing D- and L-amino acids and their derivatives and salts, particularly the N-acetyl derivatives, a preferred example of which is N-acetyl-DL-Methionine; thiols, e.g., ethane thiol; hydroxy acids, e.g., alpha-hydroxy acids such as lactic acid and glycolic acid or beta-hydroxy acids such as salicylic acid and salicylic acid derivatives such as the dodecylamide; stilbenes; hydroxystilbenes; hyaluronic acid; flavonoids; xanthones; Beta-Glucans; Skleroglucan; triterpenoid acids, e.g., arjunolic acid, ursolic acid); turmeric oil; xymeninic acid; creatine; sphingolipids such as salicycloyl-phytosphingosine, phytosphingosine, sphingosine, sphinganine and their derivatives; phytic acid; lipoic acid; lysophosphatidic acid; skin peel agents, e.g., phenol and the like); vitamin B3 compounds and retinoids.

The composition may comprise any agent that has a temporary or permanent lip plumping effect, for instance menthol, capsaicinoids, vanillyl butyl ether, capsicum, niacin, menthol, caffeine, or extracts of peppermint, ginger, clove, cinnamon, or ginseng, or a peptide based material such as for instance hexapeptide-3. Temporary lip plumping agents may optionally work by causing irritation to the lip tissue, whereas longer lasting or more permanent effects may be observed from agents that modify the collagen or moisture composition of lips.

The composition may comprise anti-inflammatory and analgesic actives. The anti-inflammatory agent can be utilized for its aesthetic and/or therapeutic benefit when topically applied to the skin. In one aspect, anti-inflammatory agents can enhance the skin appearance benefits of the present invention, e.g., such agents, contribute to a more uniform and acceptable skin tone or color. In another aspect, anti-inflammatory/analgesic agents are utilized therapeutically to reduce pain and/or swelling. Anti-inflammatory/analgesic agents can be classified into steroidal and non-steroidal agents. Specific steroidal and non-steroidal anti-inflammatory/analgesic agents useful in the composition invention include, but are not limited to, bisabolol, allantoin, phytantriol, coenzyme Q10, licorice extract, nicotinate esters, capsaicin and capsicum extracts and derivatives, glycyrrhizidine and idebenone, aspirin, ibuprofen, ketoprofen, piroxicam, flurbiprofen, naproxen, diclofenac, felbinac, and combinations thereof. The exact amount of anti-inflammatory agent to be used in the compositions will depend on the particular anti-inflammatory agent utilized since such agents vary widely in potency.

The compositions of the present invention may contain an antimicrobial or antifungal active. Such actives are capable of destroying microbes, preventing the development of microbes or preventing the pathogenic action of microbes. Examples of antimicrobial and antifungal actives include beta-lactam drugs, guanidinium compounds, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, N-octyl lactamide, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole, and combinations thereof.

Skin and Hair Conditioners

The compositions of the present invention may comprise from about 0.1% to about 50%, alternatively from about 0.5% to about 30%, alternatively from about 1% to about 20%, alternatively from about 2% to 15%, of a conditioning agent. These conditioning agents include, but are not limited to, hydrocarbon oils and waxes, silicones (volatile and nonvolitile, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof.

Non-limiting examples of hydrocarbon oils and waxes suitable for use as a conditioner include petrolatum, mineral oil, microcrystalline waxes, polyalkenes, paraffins, cerasin, ozokerite, polyethylene, perhydrosqualene, polyalphaolefins, hydrogenated polyisobutenes and combinations thereof.

Background material on silicones including sections discussing silicone fluids, gums, and resins, as well as manufacture of silicones, are found in Encyclopedia of Polymer Science and Engineering, vol. 15, 2d ed., pp 204-308, John Wiley & Sons, Inc. (1989), incorporated herein by reference. Silicone fluids suitable for use as conditioners are disclosed in U.S. Pat. Nos. 2,826,551; 3,964,500; 4,364,837; 5,104,646; 5,106,609; U.S. Reissue Pat. No. 34,584; and British Patent No. 849,433, all of which are incorporated herein by reference.

Preservatives

In one aspect, any preservative suitable for use in personal care, home care, health care, and institutional and industrial care products, can be used in the compositions of the present invention. Suitable preservatives include polymethoxy bicyclic oxazolidine, methyl paraben, ethyl paraben, propyl paraben, butyl paraben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, and suitable polyquaternium compounds disclosed above (e.g., Polyquaternium-1).

In another aspect, acid based preservatives are useful in the compositions of the present invention. The use of acid based preservatives facilitates the formulation of products in the low pH range. Lowering the pH of a formulation inherently provides an inhospitable environment for microbial growth. Moreover, formulating at low pH enhances the efficacy of acid based preservatives, and affords a personal care product which maintains an acidic pH balance on the skin as discussed by Wiechers, 2008.

Any acid based preservative that is useful in personal care, home care, health care, and institutional and industrial care products can be used in the compositions of the present invention. In one aspect, the acid preservative is a carboxylic acid compound represented by the formula: $R^{53}C(O)OH$, wherein $R^{53}$ represents hydrogen, a saturated and unsaturated hydrocarbyl group containing 1 to 8 carbon atoms or $C_6$ to $C_{10}$ aryl. In another aspect, $R^{53}$ is selected from a hydrogen, a $C_1$ to $C_8$ alkyl group, a $C_2$ to $C_8$ alkenyl group, or phenyl. Exemplary acids are, but are not limited to, formic acid, acetic acid, propionic acid, sorbic acid, caprylic acid, and benzoic acid, and mixtures thereof.

In another aspect, suitable acids include but are not limited to, oxalic acid, succinic acid, glutaric acid, adipic acid, azelaic acid, maleic acid, fumaric acid, lactic acid, glyceric acid, tartronic acid malic acid, tartaric acid, gluconic acid, citric acid, ascorbic acid, salicylic acid, phthalic acid, mandelic acid, benzilic acid, and mixtures thereof. The acid based preservatives and/or their salts can be used alone or in combination with non-acidic preservatives typically employed in personal care, home care, health care, and institutional and industrial care products.

Salts of the foregoing acids are also useful as long as they retain efficacy at low pH values. Suitable salts include the alkali metal (e.g., sodium, potassium, calcium) and ammonium salts of the acids enumerated above.

Electrolytes

The emulsion composition may contain an electrolyte. Suitable electrolytes are known compounds and include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates.

Emulsion Preparation

The O/W emulsions containing the emulsifiers of the invention can be produced by any emulsification methods known in the art. In one aspect, the emulsifier (along with the optional co-emulsifier) is dissolved or dispersed in the aqueous phase at ambient temperature with stirring and the oil phase is subsequently added to the water phase with stirring. The combined phases are sheared using a high shear impeller (e.g., dispersion blade agitators known in the art) and/or a homogenizer (e.g., a rotor stator homogenizer).

In another aspect, the procedure for the preparation of the emulsion comprises dissolving or dispersing the emulsifier according to the invention (along with the optional co-emulsifier) with stirring at ambient temperature in the oil phase and then dispersing this solution or dispersion in the aqueous phase with stirring. The combined phases are sheared using a high shear impeller (e.g., dispersion blade agitators known in the art) and/or a homogenizer (e.g., a rotor stator homogenizer).

The highly concentrated emulsions thus produced are stable against flocculation and coalescence, and have a pumpable consistency, wherein the Brookfield viscosity of the emulsions, at a spindle speed of 20 rpm, is 40,000 mPa·s or less in one aspect, 20,000 mPa·s or less in another aspect, 10,000 mPa·s or less in still another aspect, 5,000 mPa·s or less in a further aspect, 1000 mPa·s or less in still a further aspect, 500, 100, 50 mPa·s or less in an additional aspect. The emulsion is completely stable on storage even at elevated temperature (up to about 50° C.).

The O/W emulsions typically show relatively large sized emulsion droplets when viewed under an optical microscope. For example, the emulsion droplet size may be at least twice as large as the emulsion droplets in similar emulsions (based on composition and method of manufacturing) produced using an ethoxylated polymer as the emulsifier.

Alternatively, the O/W emulsions can be prepared at elevated temperature. A suitable temperature for the hot process ranges from about 30 to 95° C. in one aspect, from about 40 to 85° C. in another aspect, and from about 45 to about 75° C. in a further aspect.

In producing an O/W emulsion, the emulsifier polymer of the invention (and optional co-emulsifier) can be added as is or formulated into a pre-formed master batch as a solution or dispersion of the emulsifier in a hydrophilic liquid selected from, but not limited to, water, glycol, glycerin, and alcohol. When the emulsifier polymer is added as a master batch solution or dispersion, the amount of emulsifier polymer in the master batch solution or dispersion ranges from about 70 to about 80 wt. % in one aspect, from about 50 to about 70 wt. % in another aspect, and from about 30 to about 50 wt. % in a further aspect.

The optional components are dissolved or dispersed in either the water phase or the oil phase depending on their solubility in water or oil during the formulation of the emulsion. Determining whether an optional component is soluble or not in the water or oil phase is well within the knowledge of the formulator.

The emulsifier polymers of the invention are highly surface active, capable of reducing the surface tension by at least 15 dyne/cm, when dissolved or dispersed in water, at an amount of 0.3% by weight. By surface active is meant the ability to adsorb at an air/water or an oil/water interface, a method for evaluating which is to measure the surface tension of a dilute (typically 1% by weight) aqueous solution of a material in question. The material is surface active if the surface tension of its aqueous solution is considerably lower than that of water (72 dyne/cm).

This invention is illustrated by the following examples that are merely for the purpose of illustration and are not to be regarded as limiting the scope of the invention or the manner in which it can be practiced. Unless specifically indicated otherwise, parts and percentages are given by weight.

Methods

A. Confirmation of Polyglyceryl Branching

Carbon-13 NMR ($^{13}$C-NMR) spectroscopy allows the investigation of the microstructure of the glycerated alkyl glucoside polymers of this invention. $^{13}$C NMR spectra analysis is employed to screen for evidence of polyglyceryl branching in accordance with the technique disclosed by Sunder, A.: Hanselmann R.; Frey, H.; Mülhaupt, R. *Macromolecules* 1999, 32, 4240-4246. Sunder et al. determined the shift assignments for the linear 1,3 ($L_{1,3}$) glyceryl unit, the linear 1,4 ($L_{1,4}$) glyceryl unit and the branched glyceryl unit of a polyglyceryl compound. Shifts of δ 62.9 ppm, δ71.2 ppm and 81.6 ppm were assigned to the ($L_{1,3}$) unit; shifts of δ 70.9 ppm and δ 74.0 ppm were assigned to the ($L_{1,4}$) unit, and shifts of δ 72.5 ppm and δ 80.2 ppm were assigned to the so-called (D) unit, referred to herein as the (B) unit. The following illustrates the literature assigned carbon shifts (ppm) for linear 1,3, glyceryl unit, linear 1,4, and the branched glyceryl units of a polyglyceryl chain.

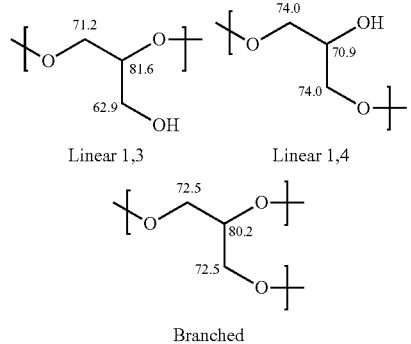

Linear 1,3　　　　Linear 1,4

Branched

The $^{13}$C-NMR spectrum for compositions of the invention are obtained in Methanol-D4 at room temperature (approximately 25° C.) on a Bruker AV 500 NMR spectrometer operating at 125.77 MHz for C-13 detection. ZGIG (inverse gated decoupling) is used for excitation with a 3 second delay between pulses (2048 scans were acquired). The sample solution is made at a concentration of 75-100 mg/0.5 mL. By comparing the $^{13}$C-NMR spectrum of a polyglyceryl component of the present invention, to the literature assigned shifts, the presence of branching can be confirmed.

B. Surface Tension Measurement

A computer controlled Krüss tensiometer (Model K100) equipped with a Krüss sw31 surface and interfacial tension measuring module controlled by LabDesk™ software (version 3.1.1., build 2623) is used for surface tension measurements. Using the above instrument, the standard Wilhelmy plate technique for measuring surface tension of aqueous solutions is used for measuring the surface tension (dyne/cm) of aqueous solutions of the polymers of the present invention. Deionized water is used in preparing all solutions used for surface tension measurements. Surface tension measurements are recorded at 1 minute intervals over a designated period of time (e.g., 5 to 30 minutes).

C. Emulsion Stability Testing

The polymer emulsifier, when used as the emulsifier for O/W emulsions, can provide for good stability of the emulsion droplets against both flocculation and coalescence. (Note that even though flocculation is a precursor to coalescence, flocculated emulsions, under certain circumstances, can remain stable against coalescence for an extended time.) This property of the emulsifier polymers of the invention can be evaluated using known methods in the art. Given that thickener free, highly concentrated emulsions typically show an increased viscosity (especially at low shear rates) when the emulsion droplets are extensively flocculated, as compared to emulsion droplets which are not highly flocculated. A method used in the present invention for evaluating emulsion stability against flocculation entails measuring the emulsion viscosity as a function of shear rate (e.g., by varying the spindle speed in a Brookfield viscometer, where higher the spindle speed equates to higher shear rate). The viscosity of a flocculated emulsion is typically lowered when the emulsion is sheared to an extent where the flocs can be broken down to smaller aggregates and/or defloculated droplets. A way to evaluate the extent of flocculation in a concentrated emulsion is to evaluate the ratios of low and high shear rate viscosities of the emulsion. Generally, the greater this ratio (often referred to as shear-thinning index), the more flocculated is the emulsion.

The stability of the emulsions against coalescence is determined using the following method: The emulsion sample is heated to 60° C. and stored at that temperature for a period of 18-24 hours, followed by centrifuging the sample at 3,000 rpm for 30 minutes. If the centrifuged emulsion shows a layer of a separated oil phase, it is classified as an unstable emulsion. A rating system is used to characterize the coalescence stability of the tested emulsions, is as follows.

i) A rating of "0" indicates no apparent signs of any oil separation at the surface of the centrifuged emulsion, and the emulsion is considered to be stable.
ii) A rating of "1" or '2" (or any intermediate values) indicates only tiny dots of the emulsified oil appearing at the surface of the centrifuged emulsion, and the emulsion is considered to be stable, given the stringent nature of the stability test used.
iii) A rating of "3" indicates large beads, still not a continuous layer, of the emulsified oil appearing at the surface of the centrifuged emulsion, the emulsion is considered to be marginally stable.
iv) A rating of "4" indicates a continuous, thin layer of the emulsified oil appearing at the surface of the centrifuged emulsion, the emulsion is considered to be unstable.
v) A rating of "5" indicates a thick layer of the emulsified oil appearing at the surface of the centrifuged emulsion, the emulsion is considered to be unstable.

Materials

Behenic Acid—obtained from Acme Hardesty Oleochemicals, Blue Bell, Pa. (used without further purification).

Glycerine Carbonate—obtained from Huntsman Co., Salt Lake City, Utah (used without further purification).

Glycidol—obtained from Aldrich Chemical Co., Milwaukee, Wis. (used without further purification).

Methyl Glucoside (MeG)—manufactured by Lubrizol Advanced Materials, Inc., Brecksville, Ohio (60 wt. % aqueous solution used as is).

Methyl Isostearate—obtained from Croda, Inc., Edison, N.J. (used as is).

Methyl Laurate—obtained from Proctor and Gamble, Cincinnati, Ohio (used as is).

Methyl Oleate—obtained from PMC Biogenix, Inc., Memphis, Tenn. (used as is).

Ricinoleic Acid—obtained from Spectrum Laboratory Products, Inc., Gardena, Calif. (used as obtained).

EXAMPLE A (SYNTHESIS OF METHYL BEHENATE)

A glass reactor equipped with a stirrer, thermometer, nitrogen inlet and water trap connected to a water cooled condenser is charged with 200 grams of Behenic acid, 150 grams of methanol, 0.4 grams of methanesulfonic acid (70%) and 0.2 grams of hypophosphorous acid (50%). The mixture is stirred and heated slowly to 130° C. to remove the water by-product along with methanol. After the distillation is stopped, the reaction mixture is treated dropwise with 150 grams of methanol under nitrogen sparge over a period of 2 hours at 130° C. to reduce the acid value to less than 1.10. The mixture is cooled to 80° C., neutralized with 0.6 grams of potassium hydroxide (45%) and stripped at 100° C. at 1 mm Hg vacuum for 15 minutes to remove water and unreacted methanol. The final produce is cooled to 80° C. and filtered through Whatman filter paper (Grade 42) to yielding 205 grams of methyl behenate as a white solid wax. GC-MS: Purity>98.7%; $^1$H-NMR (pyridine-d5): δ 0.89 ppm (t): 3H; δ 1.20-1.40 ppm (m): 36H; δ 1.65 ppm (m): 2H; δ 2.34 ppm (t): 2H; δ 3.64 ppm (s): 3H.

EXAMPLE B (SYNTHESIS OF METHYL TRI(RICINOLEATE))

A glass reactor equipped with a stirrer, thermometer, nitrogen inlet and water trap connected to a condenser is charged with 500 grams of ricinoleic acid, 1 gram of methanesulfonic acid (70%) and 0.5 grams of hypophosphorous acid (50%). The reaction mixture is stirred and heated to 140° C. under an inert nitrogen atmosphere. When the acid value drops to 65.9 the reaction mixture is immediately cooled to 125° C. and treated dropwise with 100 mL methanol under nitrogen sparge over a period of 5 hours to reduce the acid value to 0.93. The mixture is then cooled to 80° C., treated with 1.2 grams of potassium hydroxide (45%), and washed with water (2×200 mL). The final product after water separation is dried at 80° C. under 1 mmHg vacuum for 1 hour, cooled to 45° C. and filtered through Whatman filter paper (Grade 42) to yield 478 grams of methyl tri(ricinoleate) as a light yellow liquid. $^1$H-NMR (pyridine-d5): Integration area at δ 0.89 ppm (t)/Integration area at δ 3.65 ppm (s)=30.00/8.36=3.6.

EXAMPLE 1 (SYNTHESIS OF POLYGLYCERYL-20 MEG OLEATE)

A glass reactor equipped with a stirrer, thermometer, nitrogen inlet and water trap connected to a condenser is charged with 38 grams of methyl glucoside (60%) and 1 gram of sodium carbonate. The mixture is stirred and heated to 120° C. with nitrogen sparge for 30 minutes until the distillation of water stopped. The mixture is then treated dropwise with 171 grams of glycidol at 120° C. over a period of 4 hours. After the addition is complete, the mixture is held at 120° C. for 4 hours and monitored by IR until the IR absorption peak at 916 cm$^{-1}$ subsides. The mixture is cooled to 80° C., treated with 34.2 grams of methyl oleate and heated to 160° C. with nitrogen sparge. The reaction mixture is held at 160° C. and monitored by GC for the consumption of methyl oleate. After 4 hours at 160° C., methyl oleate is reduced to <0.5 wt. % of the total reaction mixture. The product is cooled to 60° C. and filtered through a 100 micron filtration bag and recovered as a single phase viscous liquid.

EXAMPLE 2 (SYNTHESIS OF POLYGLYCERYL-40 MEG OLEATE)

The same procedure described in Example 1 is employed for the synthesis of polyglyceryl-40 MeG oleate, except 24 grams of methyl glucoside (60%), 1.1 grams of sodium carbonate, 221 grams of glycidol and 22 grams of methyl oleates is utilized in the synthesis reaction.

EXAMPLE 3 (SYNTHESIS OF POLYGLYCERYL-60 MEG OLEATE)

The same procedure described in Example 1 is employed for the synthesis of polyglyceryl-60 MeG oleate, except 30 grams of methyl glucoside (60%), 2 grams of sodium carbonate, 415 grams of glycidol and 28 grams of methyl oleates is utilized in the reaction.

EXAMPLE 4 (SYNTHESIS OF POLYGLYCERYL-68 MEG OLEATE)

A glass reactor equipped with a stirrer, thermometer, nitrogen inlet and water trap connected to a condenser is charged with 18 grams of methyl glucoside (60%), 2 grams of sodium carbonate and 2 grams of hypophosphorous acid (50%). The mixture is stirred and heated to 120° C. with nitrogen sparge for 30 minutes until the distillation of water from the reaction medium is complete. The mixture was heated to 160° C. and treated dropwise with 465 grams of glycerine carbonate over a period of 12 hours. After the addition is complete, the mixture is held at 160° C. for 16 hours under a nitrogen blanket until no IR absorption peak at 1795 cm$^{-1}$ is detected. The reaction mixture is cooled to 80° C. and 17 grams of methyl oleate and 0.5 grams of sodium methylate (25 wt. % sodium methoxide in methanol) are added. The mixture is heated to 160° C. under nitrogen sparge and monitored by GC for the consumption of methyl oleate. After 4 hours at 160° C., methyl oleate is reduced to <0.5% wt. of the reaction mixture. The product is cooled to 60° C. and filtered through a 100 micron filtration bag and recovered as a single phase viscous liquid.

EXAMPLE 5 (SYNTHESIS OF POLYGLYCERYL-90 MEG OLEATE)

A glass reactor equipped with a stirrer, thermometer, nitrogen inlet and water trap connected to a condenser is charged with 12 grams of methyl glucoside (60%), 2.0 g of sodium carbonate and 2.0 grams of hypophosphorous acid. The mixture is stirred and heated to 120° C. with nitrogen for 30 minutes until the distillation of water from the reaction mixture is complete. The mixture is then treated dropwise with 248 grams of glycidol at 120° C. over a period of 9 hours. After the addition is complete, the mixture is held at 120° C. for 4 hours until no IR absorption peak at 916 cm$^{-1}$ is detected. The mixture is cooled to 80° C. and treated with 11.6 grams of methyl oleate and 0.5 grams of sodium methylate (25 wt. % sodium methoxide in methanol). The mixture is heated to 160° C. under a nitrogen blanket and monitored by GC for the consumption of methyl oleate. After 4 hours at 160° C., methyl oleate is reduced to <0.5% of the reaction mixture. The product is cooled to 60° C. and filtered through a 100 micron filtration bag and recovered as a single phase viscous liquid.

EXAMPLE 6 (SYNTHESIS OF POLYGLYCERYL-120 MEG OLEATE)

The same procedure utilized in Example 1 is used to synthesize polyglyceryl-120 MeG oleate, except 9.0 grams of methyl glucoside (60%), 1.2 grams of sodium carbonate, 250 grams of glycidol and 8.3 grams of methyl oleates are utilized. The cycle time for the complete addition of glycidol is 11 hours.

EXAMPLE 7 (SYNTHESIS OF POLYGLYCERYL-120 MEG STEARATE)

The same procedure utilized in Example 1 is used to prepare polyglyceryl-120 MeG stearate, except 8.0 grams of methyl glucoside (60%), 1.3 grams of sodium carbonate, 221 grams of glycidol and 7.6 grams of methyl stearate is employed in the reaction. The cycle time for the complete addition of glycidol is 12 hours. The cycle time for transesterification is 4 hours at 160° C.

EXAMPLE 8 (SYNTHESIS OF POLYGLYCERYL-120 MEG BEHENATE)

The same procedure utilized in Example 1 is used to prepare polyglyceryl-120 MeG behenate, except 8.0 grams of methyl glucoside (60%), 1.1 grams of sodium carbonate, 221 grams of glycidol and 8.7 grams of methyl behenate are employed in the reaction. The cycle time for the complete addition of glycidol is 12 hours. The cycle time for transesterification is 4 hours at 160° C.

EXAMPLE 9 (SYNTHESIS OF POLYGLYCERYL-120 MEG TRI(RICINOLEATE))

The same procedure utilized in Example 1 is used to prepare polyglyceryl-120 MeG tri(ricinoleate), except 8.0 grams of methyl glucoside (60%), 1.3 grams of sodium carbonate, 221 grams of glycidol and 22.0 grams of methyl tri(ricinoleate) is used in the reaction. The cycle time for the complete addition of glycidol is 12 hours. The cycle time for transesterification is 5 hours at 168° C.

EXAMPLE 10 (SYNTHESIS OF POLYGLYCERYL-20 MEG DILAURATE)

The same procedure utilized in Example 1 is used to prepare polyglyceryl-20 MeG dilaurate, except 36.0 grams of methyl glucoside (60%), 2.3 grams of sodium carbonate, 169 grams of glycidol and 49.0 grams of methyl laurate are used in the synthesis reaction. The cycle time for the complete addition of glycidol is 4 hours. The cycle time for transesterification is 5 hours at 160° C.

EXAMPLE 11 (SYNTHESIS OF POLYGLYCERYL-30 MEG DIOLEATE)

The same procedure utilized in Example 5 is used to prepare polyglyceryl-30 MeG dioleate, except 30.0 grams of methyl glucoside (60%), 1.0 gram of sodium carbonate, 0.5 grams of hypophosphorous acid, 204 grams of glycidol, 55 grams of methyl oleate and 2.0 grams of sodium methylate (25% wt. % sodium metoxide in methanol) are used in the synthesis. The cycle time for the complete addition of glycidol is 5 hours. The cycle time for transesterification is 16 hours at 165° C.

EXAMPLE 12 (SYNTHESIS OF POLYGLYCERYL-60 MEG DIOLEATE)

The same procedure utilized in Example 5 is used to prepare polyglyceryl-60 MeG dioleate, except 8.0 grams of methyl glucoside (60%), 1.4 gram of sodium carbonate, 0.7 grams of hypophosphorous acid, 112 grams of glycidol, 15 grams of methyl oleate and 1.0 grams of sodium methylate (25% wt. % sodium metoxide in methanol) are employed. The cycle time for the complete addition of glycidol is 6 hours. The cycle time for transesterification is 8 hours at 165° C.

EXAMPLE 13 (SYNTHESIS OF POLYGLYCERYL-68 MEG DIOLEATE)

A glass reactor equipped with a stirrer, thermometer, nitrogen inlet and water trap connected to a condenser is charged with 18 grams of methyl glucoside (60%), 2 grams of sodium carbonate and 2 grams of hypophosphorous acid (50%). The reaction mixture is stirred and heated to 120° C. with nitrogen sparge for 30 minutes until the distillation of water from the reaction mixture is complete. The mixture is heated to 160° C. and treated dropwise with 465 grams of glycerine carbonate over a period of 12 hours. After the addition of glycerine carbonate is completed, the mixture is held at 160° C. for 16 hours with nitrogen blanket until no IR absorption peak at 1795 $cm^{-1}$ is detected. The mixture is cooled to 80° C. and treated with 34 grams of methyl oleate and 1.0 gram of sodium methylate (25 wt. % sodium methoxide in methanol). The mixture is heated to 160° C. under nitrogen sparge and monitored by GC for the consumption of methyl oleate. After 4 hours at 160° C., methyl oleate is reduced to <0.5 wt. % of the reaction mixture. The product is then cooled to 60° C. and filtered through a 100 micron filtration bag and recovered as a single phase viscous liquid.

EXAMPLE 14 (SYNTHESIS OF POLYGLYCERYL-120 MEG DIOLEATE)

The same procedure utilized in Example 13 is used to prepare polyglyceryl-120 MeG dioleate, except 10 grams of methyl glucoside (60%), 1.7 gram of sodium carbonate, 0.8 grams of hypophosphorous acid, 465 grams of glycerine carbonate, 19 grams of methyl oleate and 1.0 grams of sodium methylate (25 wt. % sodium methoxide in methanol) are utilized. The cycle time for the complete addition of glycerine carbonate is 18 hours. The cycle time for transesterification is 8 hours at 160° C.

EXAMPLE 15 (SYNTHESIS OF POLYGLYCERYL-120 MEG TRIOLEATE)

The same procedure utilized in Example 13 is used to prepare polyglyceryl-120 MeG trioleate, except 4 grams of methyl glucoside (60%), 0.7 gram of sodium carbonate, 0.5 grams of hypophosphorous acid, 186 grams of glycerine carbonate, 11.2 grams of methyl oleate and 0.5 grams of sodium methylate (25 wt. % sodium methoxide in methanol) are used. The cycle time for the complete addition of glycerine carbonate is 18 hours. The cycle time for transesterification is 8 hours at 160° C.

EXAMPLE 16 (CHARACTERIZATION OF POLYGLYCERYL-60 METHYL GLUCOSIDE)

A glass reactor equipped with a stirrer, thermometer, nitrogen inlet and water trap connected to a condenser is charged with 8 grams of methyl glucoside (60%), 1.2 grams of sodium carbonate and 1 gram of hypophosphorous acid (50%). The reaction mixture is stirred and heated to 170° C. with nitrogen sparge for 30 minutes until the distillation of water from the reaction medium is complete. The mixture is then treated drop wise with 189 grams of glycerine carbonate at 170° C. over a period of 10 hours. After the addition is complete, the mixture is held at 170° C. for 16 hours and monitored by IR until the absorption peak at 1790 $cm^{-1}$ can no longer be detected. The final product is cooled to 60° C. and filtered through a 100-micron bag and recovered as a single phase viscous liquid. Tg (DSC): −30.10° C. MW (GPC-Light Scattering): 4517. $^1$H-NMR (pyridine-d5): 3.20-4.60 ppm (m): 310H; δ 6.00-6.80 ppm (m): 62H. $^{13}$C-NMR (MeOH-d4): δ 62.5-63.5 ppm ($L_{1,3}$); δ 70.5-71.0 ppm: ($L_{1,4}$); δ 71.0-71.5 ppm ($L_{1,3}$); δ 72.5-73.5 ppm (B); 73.5-74.5 ppm ($L_{1,4}$); δ 79.5-80.0 ppm (B); δ 81.0-82.0 ppm ($L_{1,3}$). The $^{13}$C-NMR spectrum is shown in FIG. 1.

COMPARATIVE EXAMPLE 1 (SYNTHESIS OF POLYGLYCERYL-12 METHYL GLUCOSIDE)

A glass reactor equipped with a stirrer, thermometer, nitrogen inlet and water trap connected to a condenser is charged with 40 grams of methyl glucoside (60%), 2 grams of sodium carbonate and 2 grams of hypophosphorous acid (50%). The reaction mixture is stirred and heated to 120° C. with nitrogen sparge for 30 minutes until the distillation of water from the reaction medium is complete. The mixture is then treated dropwise with 110 grams of glycidol at 120° C. over a period of 2.5 hours. After the addition is complete, the mixture is held at 120° C. for 2 hours and monitored by IR until the IR absorption peak at 916 $cm^{-1}$ can no longer be detected. The product is then cooled to 60° C. and filtered through a 100 micron filtration bag and recovered as a single phase viscous liquid. Tg (DSC): −13.31° C.

COMPARATIVE EXAMPLE 2 (SYNTHESIS OF POLYGLYCERYL-3 MEG DIOLEATE)

The same procedure utilized in Example 5 is used to prepare polyglyceryl-3 MeG dioleate, except 60.0 grams of methyl glucoside (60%), 1.0 gram of sodium carbonate, 0.5 grams of hypophosphorous acid, 41 grams of glycidol, 110.0 grams of methyl oleate and 2.4 grams of sodium methylate (25 wt. % sodium methoxide in methanol) are employed. The cycle time for the complete addition of glycidol is 1 hour. The cycle time for transesterification is 16 hours at 165° C.

COMPARATIVE EXAMPLE 3 (SYNTHESIS OF POLYGLYCERYL-10 MEG DIOLEATE)

The same procedure utilized in Example 5 is used to prepare polyglyceryl-10 MeG dioleate, except 30.0 grams of methyl glucoside (60%), 1.0 gram of sodium carbonate, 0.5 grams of hypophosphorous acid, 68 grams of glycidol, 55 grams of methyl oleate and 1.5 grams of sodium methylate (25 wt. % sodium methoxide in methanol) are used in the reaction medium. The cycle time for the complete addition of glycidol is 2 hours. The cycle time for transesterification is 16 hours at 165° C.

EXAMPLE 17

This example shows that the polyglyceryl (PGL) methyl glucoside (MeG) ester polymers of the invention are highly surface active, inasmuch as they are able to reduce the surface tension by more than 15 dyne/cm, as compared to that of water, when dissolved in aqueous solutions at an amount of 0.3% by weight of the aqueous solution. It further shows that, for a given acyl chain, the surface activity of these polymers is exceptionally high (surface tension<30 dyne/cm) when the polyglyceryl chain length is relatively long, i.e., 120 repeat units. In Table I, sodium lauryl sulfate is a well-known surface active material, and PEG-100 Stearate is as commercially available polymeric emulsifier.

TABLE 1

|  | DI Water | Test Sample | PEG-100 Stearate | PGL-20 MeG Oleate | PGL-40 MeG Oleate | PGL-60 MeG Oleate | PGL-90 MeG Oleate | PGL-120 MeG Oleate |
|---|---|---|---|---|---|---|---|---|
| Surface Tension (dyne/cm) | 72.098 | 31.987 | 46.204 | 38.164 | 34.628 | 34.946 | 30.026 | 28.711 |

Surface tension is measured using a Krüss tensiometer discussed in the methodology above. The surface tension values presented are the mean values for measurements taken over a period of five minutes at 25° C.

EXAMPLE 18

This example shows that the emulsifiers of the invention can reduce the surface tension by more than 15 dyne/cm, even when their concentration is much less than 0.1 wt. % of an aqueous solution. The surface tension values presented in Table 2 are the mean values for measurements taken over a period of five minutes at 25° C. The PGL MeG ester polymers are derived from glycidol.

TABLE 2

| Polymer (wt. %) | PGL-68 MeG Dioleate | PGL-120 MeG Oleate |
|---|---|---|
|  | Surface Tension (dyne/cm) | |
| 0.010 | 33.101 | 53.810 |
| 0.025 | 31.694 | 39.353 |
| 0.050 | 31.467 | 32.154 |
| 0.075 | 31.705 | 31.061 |
| 0.100 | 31.331 | 30.463 |
| 0.250 | 31.589 | 29.532 |
| 0.500 | 31.667 | 28.997 |
| 1.000 | 31.587 | 28.415 |

EXAMPLE 19

This example shows the effects of varying the hydrophobic components (acyl chain) of the claimed PGL MeG ester polymers, on surface activity. The surface tension measurements are carried out at 25° C. using 0.3% (w/w) polymer solutions. The surface tension values presented in Table 3 are the mean values for measurements taken over a period of five minutes. As shown in the table the oleate yields the highest surface activity (i.e., lowest surface tension), and the polyglyceryl content is relatively high, i.e., 120 repeat units. The PGL MeG ester polymers are derived from glycidol.

TABLE 3

| Test Sample | DI Water | PGL-120 MeG Oleate | PGL-120 MeG Stearate | PGL-120 MeG Triricinoleate | PGL-120 MeG Behenate |
|---|---|---|---|---|---|
| Surface Tension, (dyne/cm) | 72.1 | 28.711 | 42.5 | 42.8 | 63.5 |

EXAMPLE 20

This example shows the effects of varying the number of acyl chain of a given length, on the surface activity of the emulsifier polymers of the invention. The surface tension measurements are carried out at 25° C., using 0.3 wt. % (w/w) polymer solutions. The PGL MeG ester polymers are derived from glycerin carbonate.

TABLE 4

| Elapsed time of measurements (minute) | PGL-68 MeG Dioleate | PGL-68 MeG Oleate | PGL-120 MeG Dioleate | PGL-120 MeG Oleate | PGL-120 MeG Trioleate |
|---|---|---|---|---|---|
|  | Surface Tension (dyne/cm) | | | | |
| 1 | 32.196 | 30.567 | 30.750 | 29.298 | 31.691 |
| 2 | 31.577 | 29.984 | 30.267 | 28.627 | 31.037 |
| 3 | 31.484 | 29.918 | 30.210 | 28.522 | 30.937 |
| 4 | 31.408 | 29.906 | 30.176 | 28.476 | 30.901 |
| 5 | 31.377 | 29.854 | 30.140 | 28.439 | 30.874 |
| 6 | 31.347 | 29.857 | 30.098 | 28.403 | 30.847 |
| 7 | 31.328 | 29.813 | 30.108 | 28.374 | 30.820 |
| 8 | 31.306 | 29.793 | 30.079 | 28.359 | 30.808 |
| 9 | 31.289 | 29.798 | 30.071 | 28.339 | 30.794 |
| 10 | 31.289 | 29.779 | 30.040 | 28.325 | 30.794 |
| 11 | 31.257 | 29.747 | 30.050 | 28.298 | 30.772 |
| 12 | 31.245 | 29.740 | 30.030 | 28.305 | 30.772 |
| 13 | 31.235 | 29.737 | 30.008 | 28.305 | 30.752 |
| 14 | 31.213 | 29.725 | 30.003 | 28.293 | 30.733 |
| 15 | 31.201 | 29.732 | 30.001 | 28.310 | 30.737 |
| 16 | 31.206 | 29.742 | 29.991 | 28.281 | 30.715 |
| 17 | 31.181 | 29.720 | 29.989 | 28.298 | 30.725 |
| 18 | 31.159 | 29.706 | 29.979 | 28.283 | 30.713 |
| 19 | 31.162 | 29.715 | 29.981 | 28.269 | 30.711 |
| 20 | 31.150 | 29.693 | 29.962 | 28.269 | 30.694 |
| 21 | 31.137 | 29.688 | 29.962 | 28.271 | 30.691 |
| 22 | 31.140 | 29.710 | 29.945 | 28.264 | 30.691 |
| 23 | 31.128 | 29.696 | 29.954 | 28.271 | 30.676 |
| 24 | 31.123 | 29.684 | 29.937 | 28.247 | 30.676 |
| 25 | 31.116 | 29.686 | 29.925 | 28.249 | 30.676 |
| 26 | 31.116 | 29.696 | 29.913 | 28.247 | 30.659 |

TABLE 4-continued

| Elapsed time of measurements (minute) | PGL-68 MeG Dioleate | PGL-68 MeG Oleate | PGL-120 MeG Dioleate | PGL-120 MeG Oleate | PGL-120 MeG Trioleate |
|---|---|---|---|---|---|
| | | Surface Tension (dyne/cm) | | | |
| 27 | 31.091 | 29.674 | 29.923 | 28.239 | 30.657 |
| 28 | 31.103 | 29.693 | 29.908 | 28.266 | 30.662 |
| 29 | 31.091 | 29.654 | 29.913 | 28.249 | 30.639 |
| 30 | 31.086 | 29.652 | 29.893 | 28.227 | 30.652 |
| Mean value | 31.258 | 29.779 | 30.040 | 28.353 | 30.784 |

EXAMPLE 21

This example shows that a PGL MeG ester polymer of the present invention is more surface active than a commercially available polyoxyethylene (PEG) MeG ester polymer, where the molecular weight of the polyoxyethylene chain is comparable to the molecular weight of the polyglyceryl chain in the present polymer. Both polymers have the same acyl chains. The surface tension measurements were carried out at 25° C. The surface tension values presented in Table 5 are the mean values for the measurements taken over a period of five minutes.

TABLE 5

| Polymer (wt. %) | PGL-68 MeG Dioleate | PEG-120 MeG Dioleate* |
|---|---|---|
| 0.010 | 33.101 | 49.265 |
| 0.025 | 31.694 | 46.502 |
| 0.050 | 31.467 | 45.183 |
| 0.075 | 31.705 | 44.266 |
| 0.100 | 31.331 | 43.543 |
| 0.250 | 31.589 | 42.774 |

*comparative ethoxylated MeG Dioleate

EXAMPLE 22

This example shows that PGL MeG ester polymers of the present invention having a PGL content of at least 20 repeat units exhibits good emulsifier performance. Table 6 lists the Brookfield viscosities (at various spindle speeds) of O/W emulsions comprising 50% by weight of Isopropyl Isostearate (an ester, having a specific gravity of 0.86) as the oil phase, 7.5% by weight of an emulsifier polymer (added to the water phase), and 42.5% by weight of water. The PGL MeG ester polymers are derived from glycidol.

To ensure a relatively high level of shearing in producing the emulsions, all emulsions (100 gram samples of each) are made using a high speed homogenizer (Ika T-25 Ultra Turrax homogenizer). In making these emulsions, the oil phase is slowly added to the emulsifier solution under agitation, using a marine blade agitator. Once the addition of the oil phase is completed, the emulsion is homogenized using the homogenizer operated at 12,000 rpm for 5 minutes.

TABLE 6

| (rpm) | PGL-3 MeG Dioleate* | PGL-10 MeG Dioleate* | PGL-30 MeG Dioleate | PGL-60 MeG Dioleate | PGL-60 MeG Oleate | PGL-20 MeG Dilaurate | PEG-100 Stearate* |
|---|---|---|---|---|---|---|---|
| | | | Brookfield Viscosities (mPa · s) | | | | |
| 0.5 | 1,000 | 1,000 | 1,100 | 600 | — | 200 | 1,800 |
| 1 | 900 | 600 | 700 | 400 | 100 | 200 | 1,100 |
| 2.5 | 600 | 400 | 440 | 240 | 80 | 160 | 640 |
| 5 | 500 | 300 | 280 | 180 | 80 | 120 | 380 |
| 10 | 380 | 230 | 190 | 140 | 80 | 100 | 250 |
| 20 | 300 | 190 | 135 | 105 | 70 | 85 | 160 |

*comparative

Noting that no thickening agent was added to any of the test emulsions, higher emulsion viscosities suggest a higher level of flocculation. Accordingly, per the results shown in Table 6 it appears that the polyglyceryl (PGL) MeG ester polymers of the present invention were more effective than the prior art polymer, PEG-100 Stearate, in stabilizing the emulsions against flocculation. The lower emulsion viscosities as well as the flatter viscosity profiles versus homogenizer speed (rpm) (a measure of shear rate) suggests that the better performing emulsifiers under the test conditions utilized contain at least 20 glyceryl units.

It is also noted that even though the low shear rate (0.5 rpm) viscosities are similar for emulsions prepared from PGL-3 MeG Dioleate (comparative), PGL-10 MeG Dioleate (comparative), and PGL-30 MeG Dioleate (invention) as the emulsifier, the high shear rate (20 rpm) viscosities decreased with an increasing PGL chain length, which suggests that, during shearing (with an increasing spindle speed) of the emulsions, any flocculated aggregates ("flocs") of oil droplets broke down more easily into smaller aggregates or individual droplets when the PGL content is higher. This, in turn, suggests that PGL-30 MeG Dioleate of the invention performed better than the comparative PGL-10 MeG Dioleate which in turn performed better than the comparative PGL-3 MeG Dioleate.

EXAMPLE 23

This example shows the performance properties of various PGL MeG ester polymers of the present invention where the polymers contain 120 glyceryl repeat units, while differing in their hydrophobic component. The PGL MeG ester polymers of are derived from glycidol. As a benchmark for evaluation commercially available polymer, PEG-100 Stearate is tested alongside the invention polymers.

All emulsions (500 gram samples of each) tested contained 60% by weight of Isopropyl Isostearate as the oil phase. With all of the tested polymers, the polymer (emulsifier) dosage is varied at 2.5%, 5%, 7.5%, and 10%, based on the weight of the oil phase. The dosage of PEG-100 Stearate is varied at 5%, 7.5%, and 10%, based on the weight of the oil phase. The emulsions are made using a high shear homogenizer (Ika T-25 Ultra Turrax homogenizer). In making the emulsions, the oil phase is slowly added to the emulsifier solution under agitation with a marine blade agitator. Once the addition of the oil phase is completed, the emulsion is homogenized at 10,000 rpm for 20 minutes.

The Brookfield viscosities of the emulsions are given in Table 7. The shear thinning indices, derived from these viscosities, are given in Table 8. The shear thinning indices are set forth below. The lower the shear thinning index, the less is the extent of flocculation with loose "flocs" that break down into smaller aggregates or individual particles upon shearing of the emulsion.

TABLE 7

| Emulsion No. | Polymer | Polymer Dosage, Wt. % (based on oil) | Brookfield Viscosity (mPa · s) at Various Spindle Speeds | | | | | |
|---|---|---|---|---|---|---|---|---|
| | | | 0.5 (rpm) | 1 (rpm) | 2.5 (rpm) | 5 (rpm) | 10 (rpm) | 20 (rpm) |
| 1 | PGL-120 MeG Oleate | 2.5 | 1,920 | 1,160 | 672 | 480 | 360 | 308 |
| 2 | PGL-120 MeG Oleate | 5 | 800 | 720 | 528 | 424 | 356 | 310 |
| 3 | PGL-120 MeG Oleate | 7.5 | 1,520 | 1,280 | 928 | 720 | 568 | 472 |
| 4 | PGL-120 MeG Oleate | 10 | 2,720 | 2,160 | 1,472 | 1,136 | 904 | 736 |
| 5 | PGL-120 MeG Stearate | 2.5 | 1,280 | 960 | 688 | 560 | 452 | 378 |
| 6 | PGL-120 MeG Stearate | 5 | 3,440 | 2,360 | 1,568 | 1,208 | 920 | 670 |
| 7 | PGL-120 MeG Stearate | 7.5 | 3,840 | 2,720 | 1,776 | 1,352 | 1,064 | 820 |
| 8 | PGL-120 MeG Stearate | 10 | 5,760 | 4,000 | 2,512 | 1,912 | 1,492 | 1,160 |
| 9 | PGL-120 MeG Triricinoleate | 2.5 | 960 | 760 | 544 | 432 | 352 | 294 |
| 10 | PGL-120 MeG Triricinoleate | 5 | 640 | 560 | 448 | 400 | 352 | 316 |
| 11 | PGL-120 MeG Triricinoleate | 7.5 | 1,680 | 1,400 | 992 | 776 | 624 | 514 |
| 12 | PGL-120 MeG Triricinoleate | 10 | 5,520 | 3,880 | 2,480 | 1,808 | 1,364 | 1,068 |
| 13 | PEG-100 Stearate* | 5 | 13,200 | 8,080 | 4,000 | 2,608 | 1,680 | 1,130 |
| 14 | PEG-100 Stearate* | 7.5 | 7,920 | 5,560 | 3,552 | 2,440 | 1,660 | 1,120 |
| 15 | PEG-100 Stearate* | 10 | 8,640 | 5,680 | 3,392 | 2,328 | 1,644 | 1,100 |

*comparative

TABLE 8

| Emulsion No. (Table 7) | Shear Thinning Indices | | | |
|---|---|---|---|---|
| | STI 1[1] | STI 2[2] | STI 3[3] | STI 4[4] |
| 1 | 6.234 | 5.333 | 3.766 | 3.222 |
| 2 | 2.581 | 2.247 | 2.323 | 2.022 |
| 3 | 3.220 | 2.676 | 2.712 | 2.254 |
| 4 | 3.696 | 3.009 | 2.935 | 2.389 |
| 5 | 3.265 | 2.727 | 2.585 | 2.159 |
| 6 | 2.025 | 1.818 | 1.772 | 1.591 |
| 7 | 3.268 | 2.692 | 2.724 | 2.244 |
| 8 | 5.169 | 4.047 | 3.633 | 2.845 |
| 9 | 3.386 | 2.832 | 2.540 | 2.124 |
| 10 | 5.134 | 3.739 | 3.522 | 2.565 |
| 11 | 4.683 | 3.609 | 3.317 | 2.556 |
| 12 | 4.966 | 3.861 | 3.448 | 2.681 |
| 13 | 11.681 | 7.857 | 7.150 | 4.810 |
| 14 | 7.071 | 4.771 | 4.964 | 3.349 |
| 15 | 7.855 | 5.255 | 5.164 | 3.455 |

[1]Shear thinning Index 1 (STI 1) is defined herein as the ratio of 0.5 rpm and 20 rpm viscosities.
[2]Shear thinning Index 2 (STI 2) is defined herein as the ratio of 0.5 rpm and 10 rpm viscosities.
[3]Shear thinning Index 3 (STI 3) is defined herein as the ratio of 1 rpm and 20 rpm viscosities.
[4]Shear thinning Index 4 (STI 4) is defined herein as the ratio of 1 rpm and 10 rpm viscosities.

Based on the shear thinning index data presented in Table 8, Emulsion 2 appears to have the highest flocculation stability amongst all the emulsions made using PGL-120 MeG Oleate as the emulsifier. Likewise, Emulsions 6, 9, and 14 appear to have the highest flocculation stability amongst all the emulsions made, respectively, using PGL-120 MeG Stearate, PGL-120 MeG Triricinoleate, and PEG-100 Stearate as the emulsifier. It may be noted that the emulsifier dosage is considerably higher for Emulsion 14 than for Emulsions 2, 6, and 9.

EXAMPLE 24

This example shows that the PGL MeG ester polymers of the invention are effective emulsifiers even under high levels of an electrolyte (sodium chloride, NaCl) and under a strongly acidic pH. The PGL MeG ester polymers tested are derived from glycidol.

Test emulsions (500 gram samples of each) are made using a high shear homogenizer (Ika T-25 Ultra Turrax homogenizer). In making the emulsions, the oil phase (Isopropyl Isostearate) is slowly added to the emulsifier solution under agitation with a marine blade agitator. Once the addition of the oil phase is completed, the emulsion is homogenized at 10,000 rpm for 20 minutes. The test emulsions containing either PGL-120 MeG Stearate or PEG-100 Stearate (comparative) as the emulsifier are made at a temperature of about 70° C. A 10 wt. % (w/w) solution of hydrochloric acid is used to acidify the pH of each test emulsion. The compositions of the various test emulsions are given in Table 9.

TABLE 9

| Emulsion No. | Polymer | Oil (wt. %) | Polymer (wt. %) | Water (wt. %) | NaCl (wt. %) | Emulsion pH |
| --- | --- | --- | --- | --- | --- | --- |
| 1 | PGL-120 MeG Oleate | 50 | 5 | 45 | 0 | ** |
| 2 | PGL-120 MeG Oleate | 50 | 5 | 43 | 2 | ** |
| 3 | PGL-120 MeG Oleate | 50 | 5 | 41 | 4 | ** |
| 4 | PGL-120 MeG Triricinoleate | 50 | 5 | 45 | 0 | ** |
| 5 | PGL-120 MeG Triricinoleate | 50 | 5 | 43 | 2 | ** |
| 6 | PGL-120 MeG Triricinoleate | 50 | 5 | 41 | 4 | ** |
| 7 | PEG-100 Stearate* | 50 | 5 | 45 | 0 | *** |
| 8 | PEG-100 Stearate* | 50 | 5 | 43 | 2 | *** |
| 9 | PEG-100 Stearate* | 50 | 5 | 41 | 4 | *** |
| 10 | PGL-120 MeG Oleate | 50 | 5 | 45 | 0 | 2.2 |
| 11 | PGL-120 MeG Stearate | 50 | 5 | 45 | 0 | 2 |
| 12 | PEG-100 Stearate* | 50 | 5 | 45 | 0 | 2.15 |

*comparative

**The PGL MeG ester polymers were added as a 30% (w/w) solution at pH 7.

***PEG-100 Stearate was added as a 30% (w/w) solution, but with no prior pH adjustment.

The resulting emulsions were tested for stability against coalescence by heating the emulsions to 60° C. for about 2 hours, centrifuging the heated emulsions at 3,000 rpm for 30 minutes, and then visually inspecting the centrifuged emulsions for any oil phase separation. Given the highly stringent nature of the above stability test, an emulsion is considered unstable only if oil phase separation amounts to a separated layer of oil on the surface of the centrifuged emulsion. The emulsion is considered marginally unstable, if the oil phase separation amounts to discrete or disconnected drops (i.e., not a continuous layer) of oil appearing on the surface of the centrifuged emulsion. The emulsion is considered highly stable, if there is either no oil phase separation at all or if the oil phase separation amounted to tiny specs of oil appearing on the surface of the emulsion.

Upon stability testing of the emulsions in Table 9, as per the method described above, Emulsions 1 through 4 and Emulsions 7 through 12 were classified as being highly stable, while Emulsions 5 and 6 fell into the marginally unstable classification.

EXAMPLE 25

This example shows that highly concentrated emulsions can be more stable while less viscous, when an invention polymer, rather than a commercially available polyoxyethylated MeG ester polymer, is used as the emulsifier. The polyglyceryl content in the claimed polymer is comparable to the polyoxyethylene (PEG) content in the commercial polymer. Both polymers contain the same methyl glucose core as well as the same hydrophobic groups (i.e., dioleate). The PGL MeG ester polymer was derived from glycidol.

Highly concentrated test emulsions are prepared, based on the compositions shown in Table 10, using the following method: 500 gram emulsion samples are made by slowly adding the oil phase (Isopropyl Isostearate, density: 0.83 g/ml) to the emulsifier solution under agitation (using a Caframo mixer fitted with a 2 inch marine blade agitator, and allowing 15 minutes of mixing at 1,500 rpm), followed by further shearing of the emulsion using a 2 inch dispersion blade agitator for 20 minutes at 2,500 rpm.

TABLE 10

| Emulsion No. | Polymer | Oil (wt. %) | Polymer (wt. %) | Water (wt. %) |
| --- | --- | --- | --- | --- |
| 1 | PGL-68 MeG Dioleate | 72 | 3.6 | 24.4 |
| 2 | PGL-68 MeG Dioleate | 80 | 4 | 16 |
| 3 | PEG-120 MeG Dioleate* | 72 | 3.6 | 24.4 |
| 4 | PEG-120 MeG Dioleate* | 80 | 4 | 16 |

*comparative

The emulsions presented in Table 10 are tested for stability by comparing their Brookfield viscosities before and after they are incubated in a 60° C. oven for about 18-24 hours. The results of these Brookfield viscosity measurements are given in Table 11. Based on these results, the various shear thinning indices (STI), as defined in Example 24, are given in Table 12. The shear thinning index is used as a measure of the extent of flocculation, where a higher value of STI indicates a higher level of flocculation with loose "flocs" that break down into smaller aggregates or individual particles upon shearing of the emulsion. A higher percent change in the value of STI after incubation, relative to pre-incubation, indicates a higher instability, including that a decrease in the STI value after incubation might be due to coalescence of droplets.

TABLE 11

| (rpm) | Emulsion 1 (Table 8) | | Emulsion 2 (Table 8) | | Emulsion 3 (Table 8) | | Emulsion 4 (Table 8) | |
|---|---|---|---|---|---|---|---|---|
| | Viscosity[1] (mPa·s) | Viscosity[2] (mPa·s) | Viscosity[1] (mPa·s) | Viscosity[2] (mPa·s) | Viscosity[1] (mPa·s) | Viscosity[2] (mPa·s) | Viscosity[1] (mPa·s) | Viscosity[2] (mPa·s) |
| 0.5 | 102,000 | 128,000 | 646,000 | 572,000 | 342,000 | 521,000 | 3,590,000 | 2,580,000 |
| 1 | 58,500 | 68,400 | 404,000 | 384,000 | 190,000 | 286,000 | 2,380,000 | 1,440,000 |
| 2.5 | 28,000 | 28,160 | 196,000 | 175,000 | 89,720 | 131,000 | 1,150,000 | 690,000 |
| 5 | 16,720 | 16,400 | 112,000 | 105,000 | 52,000 | 66,000 | 633,000 | 392,000 |
| 10 | 9,920 | 9,600 | 63,700 | 59,000 | 30,520 | 38,300 | 348,000 | 228,000 |
| 20 | 5,980 | 5,740 | 36,300 | 33,800 | 18,400 | 22,450 | 200,000 | 134,000 |

[1]pre-incubation
[2]post-incubation

TABLE 12

| Emulsion No. | Pre-Incubation | | | | Post-Incubation (@ 60° C.) | | | |
|---|---|---|---|---|---|---|---|---|
| | STI 1[1] | STI 2[2] | STI 3[3] | STI 4[4] | STI 1[1] | STI 2[2] | STI 3[3] | STI 4[4] |
| 1 | 17.1 | 10.3 | 9.8 | 5.9 | 22.3 | 13.3 | 11.9 | 7.1 |
| 2 | 17.8 | 10.1 | 11.1 | 6.3 | 16.9 | 9.7 | 11.4 | 6.5 |
| 3 | 18.6 | 11.2 | 10.3 | 6.2 | 23.2 | 13.6 | 12.7 | 7.5 |
| 4 | 18.0 | 10.3 | 11.9 | 6.8 | 19.3 | 11.3 | 10.7 | 6.3 |

[1]Shear thinning Index 1 (STI 1) is defined herein as the ratio of 0.5 rpm and 20 rpm viscosities.
[2]Shear thinning Index 2 (STI 2) is defined herein as the ratio of 0.5 rpm and 10 rpm viscosities.
[3]Shear thinning Index 3 (STI 3) is defined herein as the ratio of 1 rpm and 20 rpm viscosities.
[4]Shear thinning Index 4 (STI 4) is defined herein as the ratio of 1 rpm and 10 rpm viscosities.

The results presented in Table 11 and Table 12, show that the emulsion viscosities are much lower for Emulsions 1 and 2 than for Emulsions 3 and 4, even though the flocculation stability of these emulsions do not appear to be widely different. Without limiting to any particular theory, it is speculated that the lower viscosities in Emulsions 1 and 2 are primarily due to the following: The size of the emulsion droplets are larger in Emulsions 1 and 2 than in Emulsions 3 and 4, which might be because a highly branched polymer such as a PGL MeG ester polymer would require a larger interfacial area for adsorption at an oil/water interface, as compared to a linear polymer such as PEG-120 MeG Dioleate from the prior art.

It is confirmed in subsequent experiments that in emulsions with a comparable composition and produced by the same manufacturing method, that the oil droplet size is considerably larger when PGL MeG esters are used as the emulsifier, as compared to when a polyoxyethelene based polymer (e.g., PEG-100 Stearate, PEG-120 MeG Dioleate) is used as the emulsifier.

EXAMPLE 26

This example shows that the PGL MeG ester polymers of the present invention, all derived from glycerin carbonate as the source of the polyglyceryl chain, can function as an effective emulsifier for O/W emulsions of various types of oils.

Highly concentrated test emulsions are prepared using the following method: 500 gram emulsion samples are made by slowly adding the oil phase to the emulsifier solution (at pH 7) under agitation (using a Caframo™ mixer fitted with a 2 inch dispersion blade agitator), and allowing 2 minutes of mixing at 500 rpm upon completion of oil addition, followed by further shearing of the emulsion using the dispersion blade agitator for 20 minutes at 2,500 rpm.

Three different oils, Isopropyl Isostearate, Mineral Oil, and Dimethicone (a silicone fluid), are used individually in preparing the respective O/W emulsions. The amount of oil in the foregoing emulsions was 72% by weight of the emulsions, and the emulsifier (polymer) dosages used in preparing the emulsions are 1%, 3%, and 5%, based on the weight of the oil. Additionally, a small amount of a preservative (DMDM Hydantoin, Tradename: Glydant) is added at a dosage of 0.25% by the weight of the emulsion.

These emulsions are tested for stability against flocculation and coalescence. The flocculation stability is evaluated by measuring the Brookfield viscosities of the emulsions before and after they are incubated in a 60° C. oven for about 18-24 hours. Based on the results of Brookfield viscosity measurements at various shear rates (spindle speeds), the shear thinning indices are calculated, and are given in Table 13 (for emulsions made using Isopropyl Isostearate as the oil phase), Table 14 (for emulsions made using Mineral Oil as the oil phase), and Table 15 (for emulsions made using Dimethicone as the oil phase). Based on these results, the flocculation stability is assessed as follows:

i) A higher value of STI suggests a higher level of flocculation with loose "flocs" that break down into smaller aggregates or individual particles upon shearing of the emulsion; and
 ii) A greater percent change in the value of STI after incubation, relative to pre-incubation, suggests a higher level of instability, where a reduction in the value of STI may suggest coalescence of emulsion droplets, while an increase in the value of STI suggests an increased level of flocculation.

The coalescence stability of the foregoing emulsions is evaluated by heating the emulsions to 60° C. for about 18-24 hours, centrifuging the heated emulsions at 3,000 rpm for 30 minutes, and then visually inspecting the centrifuged emulsions for any oil separation. The stability ratings for the various emulsions are given in Table 16. A rating of "0" indicates no apparent signs of any oil separation at the surface of the centrifuged emulsion, and the emulsion is considered to be stable. A rating of "1" or '2" (or any intermediate value) indicates tiny dots of the emulsified oil appearing at the surface of the centrifuged emulsion, and the emulsion is considered to be stable. A rating of "3" indicates large beads (still not a continuous layer) of the emulsified oil appearing at the surface of the centrifuged emulsion, and the emulsion is considered to be marginally unstable. A rating of "4" indicates a continuous, thin layer of the emulsified oil appearing at the surface of the centrifuged emulsion, and the emulsion is considered to be unstable. A rating of "5" indicates a thick layer of the emulsified oil appearing at the surface of the centrifuged emulsion, and the emulsion is considered to be unstable.

TABLE 13

| | (Oil: Isopropyl Isostearate) | | | | | |
|---|---|---|---|---|---|---|
| Shear | Pre-Incubation | | | Post-Incubation (@ 60° C.) | | |
| Thinning Index | 1% Polymer* | 3% Polymer* | 5% Polymer* | 1% Polymer* | 3% Polymer* | 5% Polymer* |
| Polyglyceryl (PGL)-68 Methylglucose (MeG) Dioleate | | | | | | |
| STI 1 | 23.818180 | 14.488190 | 17.745100 | 16.164380 | 16.410260 | 17.260270 |
| STI 2 | 13.681460 | 8.620500 | 10.584800 | 9.414894 | 9.733840 | 10.413220 |
| Polyglyceryl (PGL)-68 Methylglucose (MeG) Dioleate | | | | | | |
| STI 3 | 12.636360 | 10.026250 | 10.245100 | 10.091320 | 10.320510 | 9.794521 |
| STI 4 | 7.258486 | 5.968750 | 6.111111 | 5.877660 | 6.121673 | 5.909091 |
| Polyglyceryl (PGL)-120 Methylglucose (MeG) Oleate | | | | | | |
| STI $1^1$ | 23.936170 | 23.252340 | 15.334420 | 24.636360 | 22.253520 | 21.984730 |
| STI $2^2$ | 13.803680 | 13.434130 | 8.986616 | 14.188480 | 12.767680 | 12.676060 |
| STI $3^3$ | 12.606380 | 12.411210 | 10.277320 | 12.863640 | 11.830990 | 12.091600 |
| STI $4^4$ | 7.269939 | 7.170626 | 6.022945 | 7.408377 | 6.787879 | 6.971831 |
| Polyglyceryl (PGL)-120 Methylglucose (MeG) Dioleate | | | | | | |
| STI $1^1$ | 24.154590 | 15.90062 | 15.932910 | 25.280670 | 16.015780 | 17.333330 |
| STI $2^2$ | 13.850420 | 9.208633 | 9.382716 | 14.339620 | 9.248292 | 10.167600 |
| STI $3^3$ | 12.850240 | 10.26915 | 10.440250 | 13.264030 | 10.848130 | 10.809520 |
| STI $4^4$ | 7.368421 | 5.947242 | 6.148148 | 7.523585 | 6.264237 | 6.340782 |
| Polyglyceryl (PGL)-120 Methylglucose (MeG) Trioleate | | | | | | |
| STI $1^1$ | 5.120000 | 11.36951 | 18.017000 | 18.689460 | 18.302580 | 16.33333 |
| STI $2^2$ | 3.076923 | 6.727829 | 10.779660 | 10.969900 | 10.877190 | 9.949239 |
| STI $3^3$ | 4.533333 | 9.870801 | 10.311610 | 10.883190 | 10.479700 | 9.500000 |
| STI $4^4$ | 2.724359 | 5.840979 | 6.1694920 | 6.387960 | 6.228070 | 5.786802 |
| Polyethylene Glycol (PEG)-120 Methylglucose (MeG) Dioleate (prior art polymer) | | | | | | |
| STI $1^1$ | 15.490200 | 14.166670 | 20.074720 | 12.000000 | 16.919320 | 20.254780 |
| STI $2^2$ | 9.294118 | 8.530466 | 12.029850 | 7.187500 | 10.176470 | 11.507840 |
| STI $3^3$ | 9.607843 | 9.404762 | 10.809460 | 7.913043 | 10.024450 | 11.104030 |
| STI $4^4$ | 5.764706 | 5.663082 | 6.477612 | 4.739583 | 6.029412 | 6.308806 |
| Polyethylene Glycol (PEG)-100 Stearate (prior art polymer) | | | | | | |
| STI $1^1$ | 13.655590 | 14.52188 | 18.588870 | 17.714290 | 14.582130 | 17.640320 |
| STI $2^2$ | 8.464419 | 9.038787 | 11.066240 | 10.726640 | 8.861646 | 10.447760 |
| STI $3^3$ | 8.700906 | 8.455882 | 10.447760 | 9.8857140 | 8.847262 | 10.126000 |
| STI $4^4$ | 5.393258 | 5.263158 | 6.219709 | 5.9861590 | 5.376532 | 5.997286 |

*based on wt. of oil phase
[1] shear thinning Index 1 (STI 1) is defined herein as the ratio of 0.5 rpm and 20 rpm viscosities.
[2] shear thinning Index 2 (STI 2) is defined herein as the ratio of 0.5 rpm and 10 rpm viscosities.
[3] shear thinning Index 3 (STI 3) is defined herein as the ratio of 1 rpm and 20 rpm viscosities.
[4] shear thinning Index 4 (STI 4) is defined herein as the ratio of 1 rpm and 10 rpm viscosities.

TABLE 14

| | (Oil: Mineral Oil) | | | | | |
|---|---|---|---|---|---|---|
| Shear | Pre-Incubation | | | Post-Incubation (@ 60° C.) | | |
| Thinning Index | 1% Polymer* | 3% Polymer* | 5% Polymer* | 1% Polymer* | 3% Polymer* | 5% Polymer* |
| Polyglyceryl (PGL)-68 Methylglucose (MeG) Dioleate | | | | | | |
| STI $1^1$ | 21.100320 | 13.665480 | 14.624140 | 17.211160 | 13.611110 | 15.428570 |
| STI $2^2$ | 12.442750 | 8.347826 | 9.023404 | 10.384620 | 8.448276 | 9.557522 |
| STI $3^3$ | 11.521040 | 8.967972 | 8.896552 | 9.960159 | 8.333333 | 8.714286 |
| STI $4^4$ | 6.793893 | 5.478261 | 5.489362 | 6.009615 | 5.172414 | 5.398230 |
| Polyglyceryl (PGL)-120 Methylglucose (MeG) Oleate | | | | | | |
| STI $1^1$ | 20.557770 | 21.614910 | 17.330100 | 21.433450 | 22.834650 | 20.259740 |
| STI $2^2$ | 11.972160 | 12.654550 | 10.377910 | 12.560000 | 13.302750 | 11.908400 |
| STI $3^3$ | 12.031870 | 11.614910 | 9.927184 | 11.604100 | 12.125980 | 11.233770 |
| STI $4^4$ | 7.006961 | 6.800000 | 5.944767 | 6.800000 | 7.064220 | 6.603053 |

TABLE 14-continued (Oil: Mineral Oil)

| Shear Thinning Index | Pre-Incubation | | | Post-Incubation (@ 60° C.) | | |
|---|---|---|---|---|---|---|
| | 1% Polymer* | 3% Polymer* | 5% Polymer* | 1% Polymer* | 3% Polymer* | 5% Polymer* |
| Polyglyceryl (PGL)-120 Methylglucose (MeG) Dioleate | | | | | | |
| STI 1[1] | 21.508200 | 15.81395 | 15.247520 | 20.782920 | 17.301590 | 15.596330 |
| Polyglyceryl (PGL)-68 Methylglucose (MeG) Dioleate | | | | | | |
| STI 2[2] | 12.713180 | 9.503106 | 9.249249 | 12.268910 | 10.331750 | 9.444444 |
| STI 3[3] | 11.475410 | 9.715762 | 9.554455 | 11.245550 | 9.920635 | 9.174312 |
| STI 4[4] | 6.782946 | 5.838509 | 5.795796 | 6.638655 | 5.924171 | 5.555556 |
| Polyglyceryl (PGL)-120 Methylglucose (MeG) Trioleate | | | | | | |
| STI 1[1] | 19.01408 | 14.634150 | 16.000000 | 14.574900 | 14.746540 | 15.918370 |
| STI 2[2] | 11.250000 | 8.936170 | 9.741697 | 8.780488 | 8.938547 | 9.750000 |
| STI 3[3] | 10.774650 | 9.268293 | 9.454545 | 9.311741 | 9.216590 | 9.285714 |
| STI 4[4] | 6.375000 | 5.659574 | 5.756458 | 5.609756 | 5.586592 | 5.687500 |
| Polyethylene Glycol (PEG)-120 Methylglucose (MeG) Dioleate (prior art polymer) | | | | | | |
| STI 1[1] | 18.596490 | 14.31694 | 16.653700 | 14.285710 | 13.297870 | 18.643480 |
| STI 2[2] | 11.041670 | 8.704319 | 10.190480 | 8.571429 | 8.090615 | 10.961150 |
| STI 3[3] | 10.350880 | 9.071038 | 9.571984 | 8.666667 | 8.936170 | 10.365220 |
| STI 4[4] | 6.145833 | 5.514950 | 5.857143 | 5.200000 | 5.436893 | 6.094070 |
| Polyethylene Glycol (PEG)-100 Stearate (prior art polymer) | | | | | | |
| STI 1[1] | 8.192771 | 12.173000 | 17.330100 | 15.586850 | 17.678570 | 18.408810 |
| STI 2[2] | 4.956268 | 7.239649 | 10.377910 | 9.273743 | 11.392410 | 10.851370 |
| STI 3[3] | 6.457831 | 9.451477 | 9.927184 | 9.718310 | 9.928571 | 10.575280 |
| STI 4[4] | 3.906706 | 5.621079 | 5.944767 | 5.782123 | 6.398159 | 6.233766 |

*Based on wt. of oil phase
[1] shear thinning Index 1 (STI 1) is defined herein as the ratio of 0.5 rpm and 20 rpm viscosities.
[2] shear thinning Index 2 (STI 2) is defined herein as the ratio of 0.5 rpm and 10 rpm viscosities.
[3] shear thinning Index 3 (STI 3) is defined herein as the ratio of 1 rpm and 20 rpm viscosities.
[4] shear thinning Index 4 (STI 4) is defined herein as the ratio of 1 rpm and 10 rpm viscosities.

TABLE 15

(Oil: Dimethicone)

| Shear Thinning Index | Pre-Incubation | | | Post-Incubation (@t 60° C.) | | |
|---|---|---|---|---|---|---|
| | 1% Polymer* | 3% Polymer* | 5% Polymer* | 1% Polymer* | 3% Polymer* | 5% Polymer* |
| Polyglyceryl (PGL)-68 Methylglucose (MeG) Dioleate | | | | | | |
| STI 1[1] | 12.334800 | 7.088608 | 8.780488 | 11.730770 | 12.307690 | 13.629630 |
| STI 2[2] | 8.092486 | 4.955752 | 6.081081 | 4.937500 | 4.863388 | 5.118483 |
| STI 3[3] | 6.960352 | 5.189873 | 5.658537 | 7.596154 | 7.606838 | 8.000000 |
| STI 4[4] | 4.566474 | 3.628319 | 3.918919 | 4.937500 | 4.863388 | 5.118483 |
| Polyglyceryl (PGL)-120 Methylglucose (MeG) Dioleate | | | | | | |
| STI 1[1] | 13.055560 | 8.432432 | 10.579710 | 10.989010 | 10.192310 | 13.993810 |
| STI 2[2] | 8.392857 | 5.777778 | 7.053140 | 4.741784 | 4.267516 | 5.217391 |
| STI 3[3] | 7.986111 | 5.513514 | 6.521739 | 7.399267 | 6.442308 | 8.173375 |
| STI 4[4] | 5.133929 | 3.777778 | 4.347826 | 4.741784 | 4.267516 | 5.217391 |

*based on wt. of oil phase
[1] shear thinning Index 1 (STI 1) is defined herein as the ratio of 0.5 rpm and 20 rpm viscosities.
[2] shear thinning Index 2 (STI 2) is defined herein as the ratio of 0.5 rpm and 10 rpm viscosities.
[3] shear thinning Index 3 (STI 3) is defined herein as the ratio of 1 rpm and 20 rpm viscosities.
[4] shear thinning Index 4 (STI 4) is defined herein as the ratio of 1 rpm and 10 rpm viscosities.

TABLE 16

| Polymer | Oil: Isopropyl Isostearate | | | Oil: Mineral Oil | | | Oil: Dimethicone | | |
|---|---|---|---|---|---|---|---|---|---|
| | 1%* Polymer | 3%* Polymer | 5%* Polymer | 1%* Polymer | 3%* Polymer | 5%* Polymer | 1%* Polymer | 3%* Polymer | 5%* Polymer |
| PGL-68 MeG Dioleate | 4 | 2.5 | 2 | 5 | 1.5 | 1.5 | 5 | 1 | 1 |
| PGL-120 MeG Oleate | 5 | 4 | 3 | 5 | 3 | 1.5 | | | |
| PGL-120 MeG Dioleate | 4 | 2 | 2 | 5 | 2 | 1.5 | 5 | 1 | 1 |
| PGL-120 MeG Trioleate | 1.5 | 1.5 | 1.5 | 2 | 1 | 1 | — | — | — |
| PEG-120 MeG Dioleate | 2.5 | 2.5 | 2.5 | 3 | 1.5 | 2 | — | — | — |
| PEG-100 Stearate | 1.5 | 1.5 | 1 | 2.5 | 2 | 1.5 | — | — | — |

*polymer wt. % based on the weight of the oil phase component

As evident from Table 16, the PGL MeG ester polymers of the present invention can be used as the emulsifier to produce stable O/W emulsions of various types of oil.

EXAMPLE 27

This example shows that relatively stable O/W emulsions of a vegetable oil and sunflower oil can be produced using the PGL MeG ester polymers of the present invention as the emulsifier in combination with a low HLB surfactant. Stable O/W emulsions are generally difficult to prepare with sunflower oil in the absence of a low HLB co-emulsifier.

200 gram samples of O/W emulsions, containing 72 wt. % of sunflower oil, are prepared following the method described below. The required amount of sunflower oil, with or without a low HLB surfactant pre added to it, is slowly added to the aqueous emulsifier solution (at pH 7) under agitation with a dispersion blade agitator fitted to a Caframo mixer. The amount of the emulsifier is 5%, based on the weight of sunflower oil. The resulting mixture is sheared for 20 minutes at a mixing speed of 1,500-2,500 rpm. In preparing emulsions, where the low HLB emulsifier was Methylglucose Sesquistearate, both the emulsifier solution and the oil phase are first individually heated to 65-70° C., and the mixing of the two phases and the subsequent shearing of the emulsion is carried out at 65-70° C.

The coalescence stability of the foregoing emulsions are evaluated by heating the emulsions to 60° C. for about 18-24 hours, centrifuging the heated emulsions at 3,000 rpm for 30 minutes, and then visually inspecting the centrifuged emulsions for any oil-separation. The stability ratings for the various emulsions are defined in Example 26.

Without wishing to be limited to any particular theory, it is speculated that a vegetable oil, which typically contains an amount of free fatty acids, may tend to act akin to a self-emulsifying oil under the emulsifying influence of the fatty acids, wherein the droplets produced upon shearing of an oil/water mixture are relatively small in size. The small size of these emulsion droplets render it difficult for a PGL MeG ester polymer to bind/adsorb onto the droplets at an adequate amount in order to provide for emulsion stability. The greater the PGL content, the more difficult it may be for the polymer to adsorb onto the oil droplets. The presence of a low HLB surfactant in the oil phase may counter the foregoing effect due to any free fatty acids in the oil phase, inasmuch as the oil droplets produced upon shearing of the oil phase in the water phase (emulsifier solution), may be large enough (due to its inherent tendency to invert an oil-in-water emulsion to a water-in-oil emulsion) for an easier adsorption of the PGL MeG ester polymers.

TABLE 17

| Polymer | Low-HLB Surfactant: Sorbitan Oleate (HLB = 4.3) | | | | Low-HLB Surfactant: Methylglucose Dioleate (HLB = Expected to be <3) | | | Low-HLB Surfactant: Methylglucose Sesquistearate (HLB = 6.6) | | |
|---|---|---|---|---|---|---|---|---|---|---|
| | 0.5% on weight of oil | 1% on weight of oil | 3% on weight of oil | 5% on weight of oil | 1% on weight of oil | 3% on weight of oil | 5% on weight of oil | 1% on weight of oil | 3% on weight of oil | 5% on weight of oil |
| PGL-68 MeG Dioleate | 0.5 | 1.5 | 3 | 3 | 2 | 3 | 4 | 4 | 4 | 5 |
| PGL-120 MeG Oleate | | 4 | 4 | 5 | 4 | 3.5 | 4 | 4 | 5+ | 5+ |

What is claimed is:

1. An esterified branched polyglyceryl ether of an alkyl glucoside having one or more polyglyceryl moieties and one or more acyl moieties, wherein all of said one or more acyl moieties are situated on said one or more polyglyceryl moieties via an ester linkage, wherein said alkyl glucoside is represented by the formula:

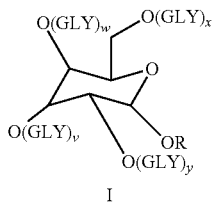

wherein R represents an alkyl group containing 1 to 22 carbon atoms; GLY is a substituted or unsubstituted glyceryl or polyglyceryl residue represented by the formulae:

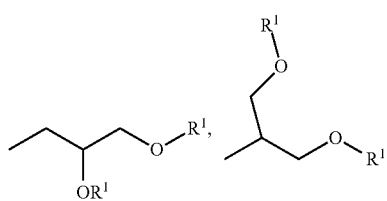

and combinations thereof, wherein $R^1$ can be the same or different and is selected from hydrogen, an acyl group containing 8 to 54 carbon atoms, and GLY, wherein GLY is as defined above, the sum of v+w+x+y is an integer ranging from about 20 to about 150, subject to the proviso that a portion of $R^1$ represents said acyl group, and wherein the average degree of glyceryl substitution ($DS_g$) on the alkyl glucoside is about 4.

2. The esterified polyglyceryl alkyl glucoside of claim 1 wherein GLY contains a terminal glyceryl moiety represented by the formulae:

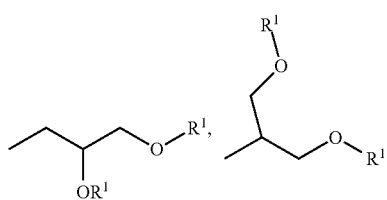

wherein $R^1$ is selected from hydrogen, an acyl group containing 8 to 54 carbon atoms, and combinations thereof, and wherein at least one of $R^1$ is said acyl group.

3. The esterified polyglyceryl alkyl glucoside of claim 1 wherein the total degree of acyl substitution ($DS_a$) ranges from about 1 to about 4.

4. The esterified polyglyceryl alkyl glucoside of claim 1 wherein the total degree of acyl substitution ($DS_a$) ranges from about 1 to about 3.

5. The esterified polyglyceryl alkyl glucoside of claim 1 wherein the total degree of acyl substitution ($DS_a$) is about 2.

6. The esterified polyglyceryl alkyl glucoside of claim 1 wherein the total degree of acyl substitution ($DS_a$) is about 1.

7. The esterified polyglyceryl alkyl glucoside of claim 1 wherein said acyl group contains unsaturation.

8. The esterified polyglyceryl alkyl glucoside of claim 1 wherein said acyl group is a residue of a fatty acid selected from caprylic acid, capric acid, lauric acid, myristic acid, palmitic acid, palmitoleic acid, stearic acid, oleic acid, vaccenic acid, linoleic acid, alpha-linolenic acid, gamma-linolenic acid, eicosanoic acid, 9-eicosenoic acid, 5,8,11,14-eicosatetraenoic acid, 5,8,11,14,17-eicosapentaenoic acid, behenic acid, erucic acid, 4,7,10,13,16,19-docosahexaenoic acid, lignoceric acid, triricinoleic acid, or combinations thereof.

9. The esterified polyglyceryl alkyl glucoside of claim 1 wherein said acyl group is a residue of oleic acid.

10. The esterified polyglyceryl alkyl glucoside of claim 1 wherein the sum of v+w+x+y is an integer ranging from about 40 to about 140.

11. The esterified polyglyceryl alkyl glucoside of claim 10 wherein the sum of v+w+x+y is an integer ranging from about 60 to about 120.

12. The esterified polyglyceryl alkyl glucoside of claim 11 wherein the sum of v+w+x+y ranges from about 65 to about 75.

13. An esterified branched polyglyceryl ether of an alkyl glucoside prepared by a process of:
(A) reacting an alkyl glucoside of the formula:

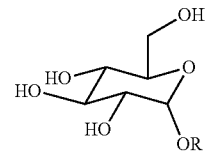

wherein R represents an alkyl group containing 1 to 10 carbon atoms with glycidol or glycerin carbonate to obtain a branched polyglyceryl alkyl glucoside of the formula:

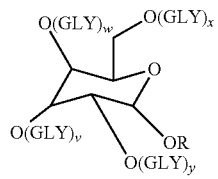

wherein R is as defined as above; GLY is the same or different and is selected from hydrogen and a glyceryl or polyglyceryl residue represented by the formula:

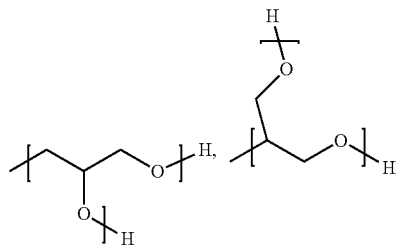

wherein the sum of v+w+x+y is an integer ranging from about 20 to about 150 and the total degree of glyceryl substitution ($DS_g$) is about 4; and
(B) reacting the branched polyglyceryl alkyl glucoside obtained in step (A) with an acylating agent to obtain an acyl substituted polyglyceryl alkyl glucoside wherein a portion of the hydroxyl groups on said polyglyceryl alkyl glucoside are acylated.

14. The method of claim 13 wherein the total degree of acyl substitution ($DS_a$) on the glyceryl moieties ranges from about 1 to about 4.

15. The method of claim 14 wherein the total degree of acyl substitution ($DS_a$) on the glyceryl moieties ranges from about 1 to about 3.

16. The method of claim 15 wherein the total degree of acyl substitution ($DS_a$) on the glyceryl moieties ranges from about 1 to about 2.

17. The method of claim 13 wherein said acylating agent is selected from a fatty acid containing 8 to 54 carbon atoms.

18. The method of claim 17 wherein said acylating agent contains unsaturation.

19. The method of claim 17 wherein said acylating agent is selected from caprylic acid, capric acid, lauric acid, myristic acid, palmitic acid, palmitoleic acid, stearic acid, oleic acid, vaccenic acid, linoleic acid, alpha-linolenic acid, gamma-linolenic acid, eicosanoic acid, 9-eicosenoic acid, 5,8,11,14-eicosatetraenoic acid, 5,8,11,14,17-eicosapentaenoic acid, behenic acid, erucic acid, 4,7,10,13,16,19-docosahexaenoic acid, lignoceric acid, and combinations thereof.

20. The method of claim 18 wherein said acylating agent is oleic acid.

21. The method of claim 13 wherein the sum of v+w+x+y ranges from about 40 to about 140.

22. The method of claim 21 wherein the sum of v+w+x+y ranges from about 60 to about 120.

23. The method of claim 22 wherein the sum of v+w+x+y ranges from about 65 to about 100.

24. An O/W emulsion composition comprising:
   (i) an effective stabilizing amount of a polyglyceryl alkyl glucoside of claim 1;
   (ii) an oily phase;
   (iii) an aqueous phase; and optionally
   (iv) a coemulsifier.

25. The O/W emulsion of claim 24 wherein said oily phase component is selected from vegetable oils, animal oils, hydrocarbon oils, fatty alcohols, fatty acid esters, silicone oils, oily UV absorbers and sunscreens, fragrance oils, and mixtures thereof.

26. The O/W emulsion of claim 24 wherein said co-emulsifier is selected from low HLB emulsifier ranging from about 1 to about 7.

27. The O/W emulsion of claim 24 wherein said co-emulsifier is selected from sorbitan esters, glyceryl esters, polyglyceryl esters, glycol esters, sucrose esters, methyl glucose esters, ethoxylated methyl glucose esters, or mixtures thereof.

28. The O/W emulsion of claim 24 wherein said co-emulsifier is selected from sorbitan laurate, sorbitan palmitate, sorbitan sesquiisostearate, sorbitan sesquioleate, sorbitan sesquistearate, sorbitan stearate, sorbitan oleate, sorbitan monoisostearate, sorbitan trisostearate, sorbitan trioleate, sorbitan tristearate; glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate; polyglyceryl-4 isostearate, polyglyceryl-3 oleate, polyglyceryl-2 sesquioleate, triglyceryl diisostearate, diglyceryl monooleate, tetraglyceryl monooleate, glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate; sucrose cocoate, sucrose laurate; Methyl Glucose Sesquistearate, Methyl Glucose Dioleate; PEG-20 Methyl Glucose Sesquistearate; or mixtures thereof.

29. The O/W emulsion of claim 24 further comprising a benefit agent.

30. The O/W emulsion of claim 29 wherein said benefit agents is selected from fragrances, perfumes, botanicals, particulate materials, exfoliants, anti-dandruff agents, insoluble materials, opacifiers and pearlizing agents, humectants, emollients, antioxidants, deodorizing agents, pH adjusting agents, buffers, chelation agents, viscosity modifiers, structuring agents, deposition aids, and topically active compounds such as UV protection agents, sunscreens, insect repellents, antiperspirants, cosmeceuticals, pharmaceuticals, skin and hair conditioners, preservatives, and combinations thereof.

31. The O/W emulsion of claim 24 wherein the volume fraction of the oil phase ranges from about 0.01 to about 0.95, based on the total volume of the oil and water in the emulsion.

32. The O/W emulsion of claim 24 wherein the weight of the oil phase ranges from about 1 to about 95 wt. %, based on the total weight of the oil, water and emulsifier components in the emulsion.

\* \* \* \* \*